US012613337B2

(12) United States Patent　　　(10) Patent No.:　US 12,613,337 B2
Iwasaki et al.　　　　　　　　　　(45) Date of Patent:　Apr. 28, 2026

(54) ULTRASOUND DIAGNOSIS APPARATUS TO CORRECT A SATURATION REGION IN AN ULTRASOUND IMAGE

(71) Applicant: CANON MEDICAL SYSTEMS CORPORATION, Otawara (JP)

(72) Inventors: Ryosuke Iwasaki, Otawara (JP); Hiroki Takahashi, Nasushiobara (JP); Tomohisa Imamura, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 18/451,421

(22) Filed: Aug. 17, 2023

(65) Prior Publication Data

US 2024/0061109 A1　　Feb. 22, 2024

(30) Foreign Application Priority Data

Aug. 18, 2022　(JP) ................................. 2022-130567

(51) Int. Cl.
　　*G01S 15/89*　　　(2006.01)
　　*A61B 8/00*　　　　(2006.01)
(52) U.S. Cl.
　　CPC ........ *G01S 15/8977* (2013.01); *A61B 8/5207* (2013.01)
(58) Field of Classification Search
　　CPC ............. G01S 7/52038; G01S 7/52046; G01S 7/52026; A61B 8/5269
　　See application file for complete search history.

(56) References Cited

U.S. PATENT DOCUMENTS

| | | | |
|---|---|---|---|
| 2006/0173340 A1 | 8/2006 | Umemura | |
| 2009/0105585 A1* | 4/2009 | Wang | ................... A61B 8/4455 |
| | | | 600/437 |
| 2012/0082359 A1 | 4/2012 | Arditi et al. | |
| 2013/0004047 A1* | 1/2013 | Shiki | ................... G01S 7/52033 |
| | | | 382/131 |
| 2014/0066768 A1* | 3/2014 | Sui | ...................... G01S 15/8915 |
| | | | 600/443 |
| 2017/0071569 A1 | 3/2017 | Sato | |
| 2017/0071575 A1 | 3/2017 | Sato | |
| 2017/0224310 A1* | 8/2017 | Fuse | ........................ A61B 8/54 |

(Continued)

FOREIGN PATENT DOCUMENTS

| | | |
|---|---|---|
| JP | 2004-275491 A | 10/2004 |
| JP | 2012-529320 A | 11/2012 |

(Continued)

OTHER PUBLICATIONS

Extended European Search Report issued Jan. 3, 2024 in European Patent Application No. 23192027.3, 8 pages.

*Primary Examiner* — Nyrobi Celestine
(74) *Attorney, Agent, or Firm* — Oblon, McClelland, Maier & Neustadt, L.L.P.

(57) ABSTRACT

An ultrasound diagnosis apparatus according to an embodiment includes processing circuitry. The processing circuitry is configured to detect a saturation region of a signal based on an ultrasound wave received by an ultrasound probe; and to correct a first signal including an odd-numbered order harmonic component of the saturation region, on a basis of a second signal including an even-numbered order harmonic component of the saturation region.

9 Claims, 14 Drawing Sheets

(56)                        References Cited

U.S. PATENT DOCUMENTS

| | | | |
|---|---|---|---|
| 2019/0159750 A1 | 5/2019 | Sato | |
| 2019/0159763 A1* | 5/2019 | Sato ......................... | A61B 8/14 |
| 2020/0163653 A1* | 5/2020 | Taniguchi ........... | G01S 15/8915 |
| 2022/0015743 A1* | 1/2022 | Taniguchi .............. | A61B 8/085 |

FOREIGN PATENT DOCUMENTS

| | | |
|---|---|---|
| JP | 2013-351 A | 1/2013 |
| JP | 2016-112400 A | 6/2016 |
| JP | 2017-55845 A | 3/2017 |
| JP | 2017-55846 A | 3/2017 |
| JP | 2019-97794 A | 6/2019 |
| JP | 2019-97795 A | 6/2019 |

* cited by examiner

TI1

SATURATION REGION

SATURATION REGION

ULTRASOUND DIAGNOSIS APPARATUS TO CORRECT A SATURATION REGION IN AN ULTRASOUND IMAGE

CROSS-REFERENCE TO RELATED APPLICATIONS

This application is based upon and claims the benefit of priority from Japanese Patent Application No. 2022-130567, filed on Aug. 18, 2022, the entire contents of which are incorporated herein by reference.

FIELD

Embodiments described herein relate generally to an ultrasound diagnosis apparatus, an image processing apparatus, and a computer program product.

BACKGROUND

Ultrasound diagnosis apparatuses are medical image equipment configured to non-invasively obtain a tomographic image of a soft tissue in a patient's body through the body surface, by implementing an ultrasound pulse reflection method. Ultrasound diagnosis apparatuses have advantages over other medical image equipment for being more compact, less expensive, and safer without exposure to radiation such as X-rays, and also being capable of imaging blood flows and are widely used on the heart, the abdomen, and the urinary organs and in obstetrics and gynecology departments, and the like.

Further, in recent years, for diagnosing purposes, harmonic wave imaging (hereinafter, "harmonic imaging") such as Tissue Harmonic Imaging (THI) is used by which a harmonic component occurring due to a non-linear phenomenon of ultrasound propagation in the patient's body is expressed in a picture. A harmonic wave used in such harmonic imaging has a lower sidelobe level than that of a fundamental wave. For this reason, harmonic imaging is able to enhance image quality of ultrasound images, as compared to conventional techniques using a fundamental wave. For example, harmonic imaging is able to acquire an image having excellent azimuth and contrast resolutions, without missing blood vessels and the like from the image. Known for such harmonic imaging is, for example, a third harmonic imaging method that uses a third harmonic wave.

BRIEF DESCRIPTION OF THE DRAWINGS

FIG. 5 is a chart for explaining an example of a flow of processes including a replacement process according to the first embodiment;

FIG. 6 is a drawing for explaining an example of processes including a signal value offset calculating process according to the first embodiment;

FIG. 11 is a drawing for explaining an example of a flow of processes including a blending process according to the second embodiment;

DETAILED DESCRIPTION

An ultrasound diagnosis apparatus according to an embodiment includes processing circuitry. The processing circuitry is configured to detect a saturation region of a signal based on an ultrasound wave received by an ultrasound probe; and to correct a first signal including an odd-numbered order harmonic component of the saturation region, on the basis of a second signal including an even-numbered order harmonic component of the saturation region.

Exemplary embodiments of an ultrasound diagnosis apparatus, an image processing apparatus, and a computer program product will be explained in detail below, with reference to the accompanying drawings.

First Embodiment

Figure 1:
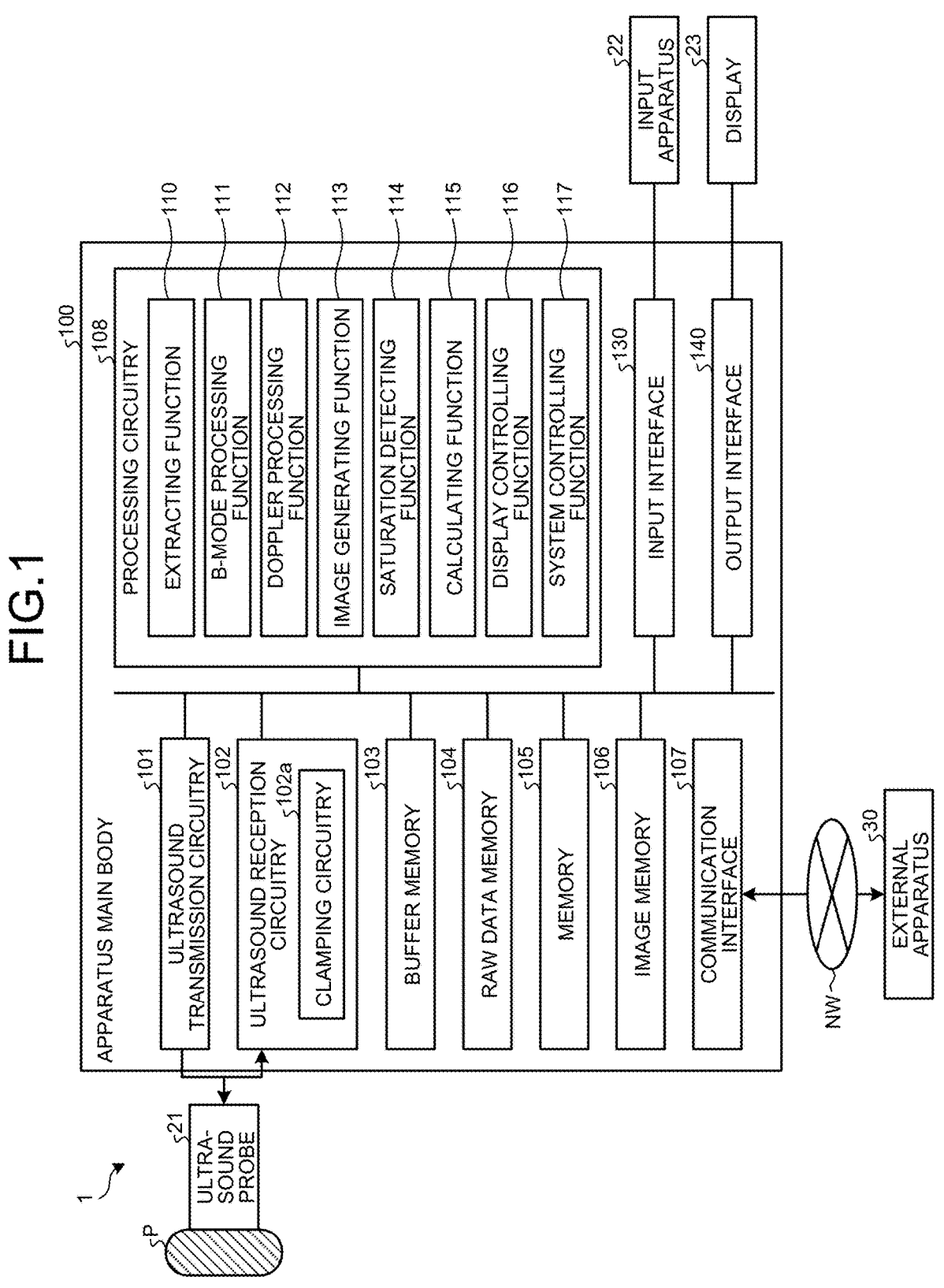
FIG. 1 is a block diagram illustrating an exemplary configuration of an ultrasound diagnosis apparatus according to a first embodiment.

FIG. 1 is a block diagram illustrating an example of an ultrasound diagnosis apparatus 1 according to a first embodiment. As illustrated in FIG. 1, the ultrasound diagnosis apparatus 1 includes an apparatus main body 100, an ultrasound probe 21, an input apparatus 22, and a display 23. Further, the apparatus main body 100 is connected to an external apparatus 30 via a network NW.

The ultrasound probe 21 includes a plurality of elements such as piezoelectric transducer elements, for example. The plurality of elements are configured to generate an ultrasound wave on the basis of a drive signal supplied from ultrasound transmission circuitry 101 included in the apparatus main body 100.

Further, the ultrasound probe 21 is configured to receive a reflected wave coming from an examined subject (hereinafter, "patient") P and to convert the reflected wave into an electric signal. Further, the ultrasound probe 21 includes, for example, a matching layer provided for the piezoelectric transducer elements, a backing material configured to prevent ultrasound waves from propagating rearwards from the piezoelectric transducer elements, and the like. In this situation, the ultrasound probe 21 is detachably connected to the apparatus main body 100.

When an ultrasound wave is transmitted from the ultrasound probe 21 to the patient P, the transmitted ultrasound wave is repeatedly reflected on a surface of discontinuity of acoustic impedances at a tissue in the body of the patient P and is received as a reflected-wave signal by the plurality of elements included in the ultrasound probe 21. The amplitude of the received reflected-wave signal is dependent on the difference between the acoustic impedances on the surface of discontinuity on which the ultrasound wave is reflected.

When a transmitted ultrasound pulse is reflected on the surface of a moving blood flow, a cardiac wall, or the like, the reflected-wave signal is, due to the Doppler effect, subject to a frequency shift, depending on a velocity component of the moving objects with respect to the ultrasound wave transmission direction. Further, the ultrasound probe 21 is configured to output the reflected-wave signal to ultrasound reception circuitry 102 included in the apparatus main body 100.

In the present embodiment, the ultrasound probe 21 is assumed to be a one-dimensional array probe in which the plurality of ultrasound transducer elements are arranged along a predetermined direction; however, the ultrasound probe 21 does not necessarily have to be a one-dimensional array probe.

For example, when being capable of obtaining volume data, the ultrasound probe 21 may be a two-dimensional array probe (a probe in which the plurality of ultrasound transducer elements are arranged in a two-dimensional matrix formation) or a mechanical four-dimensional (4D) probe (a probe capable of performing an ultrasound scan while mechanically swinging an ultrasound transducer element array in a direction orthogonal to the array direction).

For example, the input apparatus 22 is realized by using input means such as a mouse, a keyboard, a button, a panel switch, a touch command screen, a foot switch, a trackball, a joystick, and/or the like. The input apparatus 22 is configured to receive various types of setting requests from an operator of the ultrasound diagnosis apparatus 1 and to transfer the received various types of setting requests to the apparatus main body 100.

For example, the display 23 is configured to display a Graphical User Interface (GUI) used by the operator of the ultrasound diagnosis apparatus 1 for inputting the various types of setting requests via the input apparatus 22 and to display an ultrasound image represented by ultrasound image data generated by the apparatus main body 100, and the like. The display 23 is realized by a liquid crystal monitor, an Organic Light Emitting Diode (OLED) monitor, or the like.

The apparatus main body 100 is configured to generate the ultrasound image data on the basis of the reflected-wave signal received by the ultrasound probe 21. The apparatus main body 100 is capable of generating two-dimensional ultrasound image data on the basis of reflected-wave data corresponding to a two-dimensional region of the patient P and having been received by the ultrasound probe 21. Also, the apparatus main body 100 is capable of generating three-dimensional ultrasound image data on the basis of reflected-wave data corresponding to a three-dimensional region of the patient P and having been received by the ultrasound probe 21.

As illustrated in FIG. 1, the apparatus main body 100 includes the ultrasound transmission circuitry 101, the ultrasound reception circuitry 102, a buffer memory 103, a raw data memory 104, a memory 105, an image memory 106, a communication interface 107, processing circuitry 108, an input interface 130, and an output interface 140.

The ultrasound transmission circuitry 101 is configured to cause the ultrasound probe 21 to transmit the ultrasound wave under control of the processing circuitry 108. The ultrasound transmission circuitry 101 includes, for example, trigger generating circuitry, delay circuitry, pulser circuitry (not illustrated), and the like. The trigger generating circuitry is configured to repeatedly generate a trigger pulse used for forming a transmission ultrasound wave at a predetermined rate frequency fr Hz (cycle: 1/fr second).

Further, the delay circuitry is configured to apply, to each trigger pulse, a delay time period required to converge the ultrasound wave into the form of a beam and to determine transmission directionality with respect to each channel. The pulser circuitry is configured to apply a drive pulse to the ultrasound probe 21 with timing based on the trigger pulses.

The ultrasound reception circuitry 102 is configured to generate the reflected-wave data on the basis of the reflected-wave signal received by the ultrasound probe 21. Further, the ultrasound reception circuitry 102 is configured to store the generated reflected-wave data into the buffer memory 103.

More specifically, after having reached the piezoelectric transducer elements inside the ultrasound probe 21, the reflected wave of the ultrasound wave transmitted by the ultrasound probe 21 is converted by the piezoelectric transducer elements from mechanical vibration into an electrical signal (the reflected-wave signal), so as to be input to the ultrasound reception circuitry 102.

The ultrasound reception circuitry 102 includes, for example, a pre-amplifier, an Analog to Digital (A/D) converter, quadrature detection circuitry, and the like and is configured to generate the reflected-wave data by performing various types of processes on the reflected-wave signal received by the ultrasound probe 21.

The pre-amplifier is configured to perform a gain adjustment process (a gain correction) by amplifying the reflected-wave signal with respect to each channel. The A/D converter is configured to convert the gain-corrected reflected-wave signal into a digital signal, by performing an A/D conversion on the gain-corrected reflected-wave signal. The quadrature detection circuitry is configured to convert the reflected-wave signal resulting from the A/D conversion into an In-phase signal (an I signal) and a Quadrature-phase signal (a Q signal) in the baseband.

Further, the quadrature detection circuitry is configured to store the I signal and the Q signal into the buffer memory 103 as the reflected-wave data. In the following sections, the I signal and the Q signal may collectively be referred to as IQ signals. Further, because the IQ signals are represented by digital data resulting from the A/D conversion, the IQ signals may be referred to as IQ data. The IQ data is complex signal data having amplitude information and phase information.

The ultrasound reception circuitry 102 is configured to generate two-dimensional reflected-wave data from a two-dimensional reflected-wave signal received by the ultrasound probe 21. Alternatively, the ultrasound reception circuitry 102 may generate three-dimensional reflected-wave data from a three-dimensional reflected-wave signal received by the ultrasound probe 21.

Further, the ultrasound reception circuitry 102 includes clamping circuitry 102a. The clamping circuitry 102a is configured to protect the ultrasound reception circuitry 102 from reflected-wave signals having excessively large amplitude.

For example, the clamping circuitry 102a is circuitry structured with: a diode of which an anode is connected to a transmission path passing the reflected-wave signal and of which a cathode is connected to the ground; and another diode of which a cathode is connected to a transmission path passing the reflected-wave signal and of which an anode is connected to the ground. Upon receipt of an input of a reflected-wave signal exceeding a prescribed value, the clamping circuitry 102a is configured to perform a clamping process by clipping (fixing) a signal part exceeding the prescribed value so as to have the prescribed value, for the purpose of protecting the ultrasound reception circuitry 102.

In relation to the above, it is known that a saturation phenomenon occurs to the reflected-wave signal when the clamping circuitry 102a is in operation. In the following sections, a relationship between operations of the clamping circuitry 102a and the saturation phenomenon will be explained, with reference to FIGS. 2 and 3.

Figure 2:
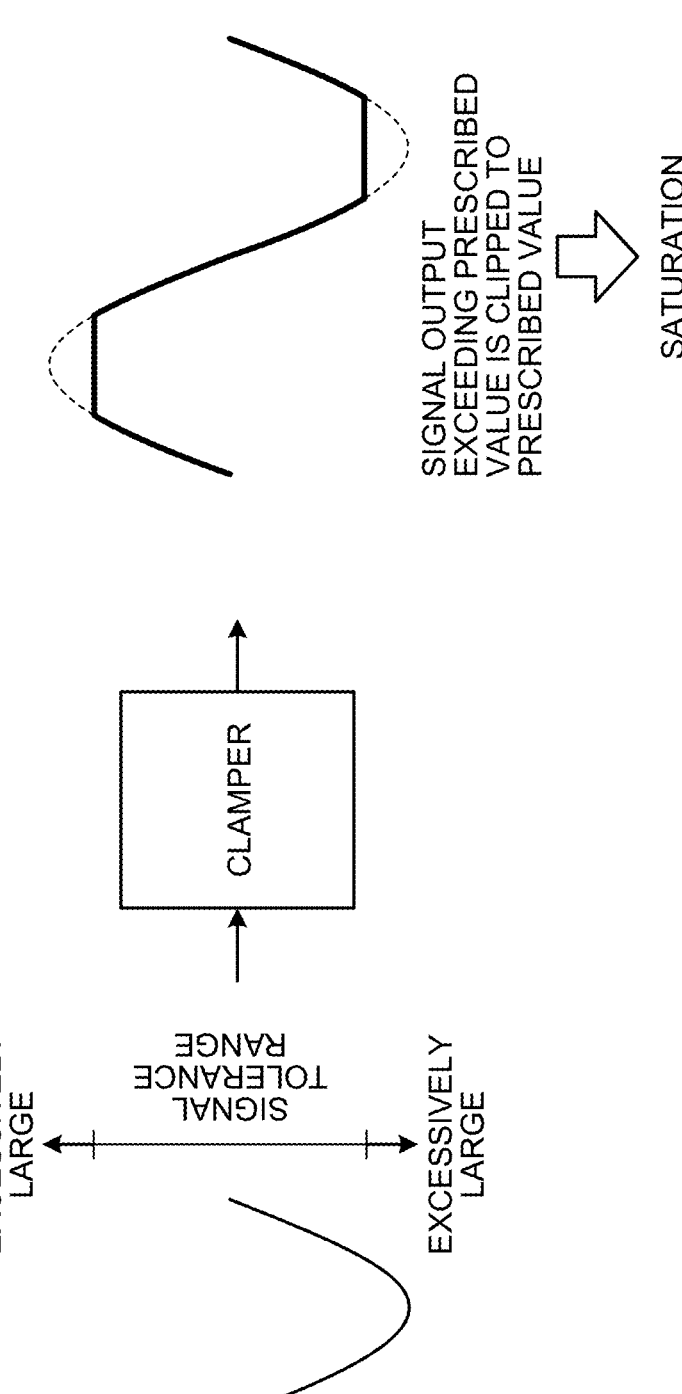
FIG. 2 is a drawing for explaining an example of a relationship between an operation of clamping circuitry according to the first embodiment and a saturation phenomenon.
Figure 3:
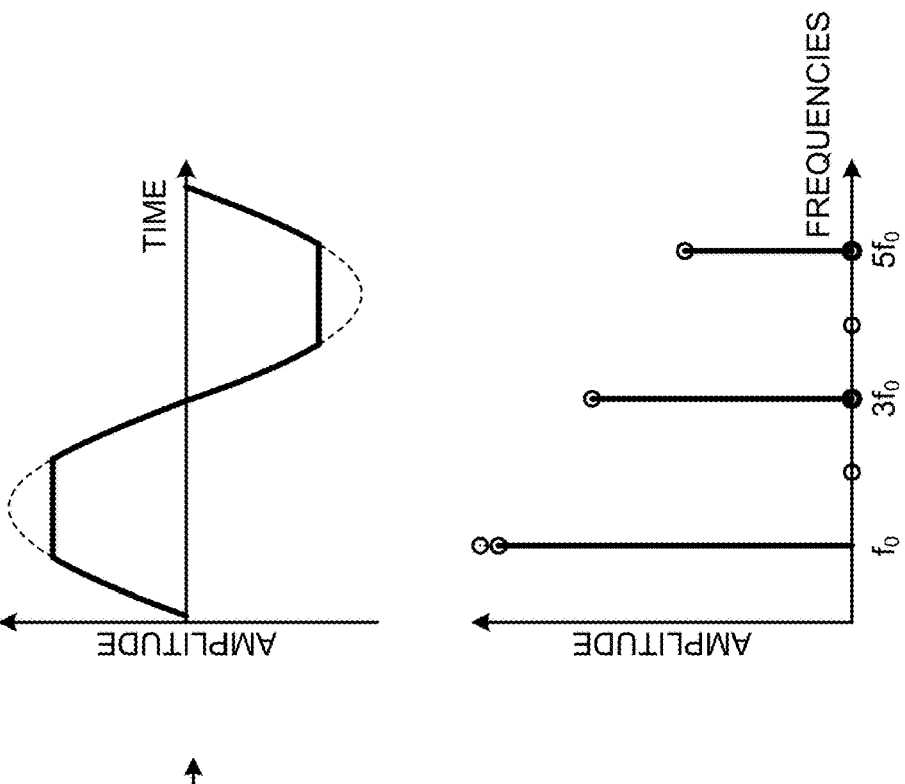
FIG. 3 is another drawing for explaining the example of the relationship between the operation of the clamping circuitry according to the first embodiment and the saturation phenomenon.
Figure 3:
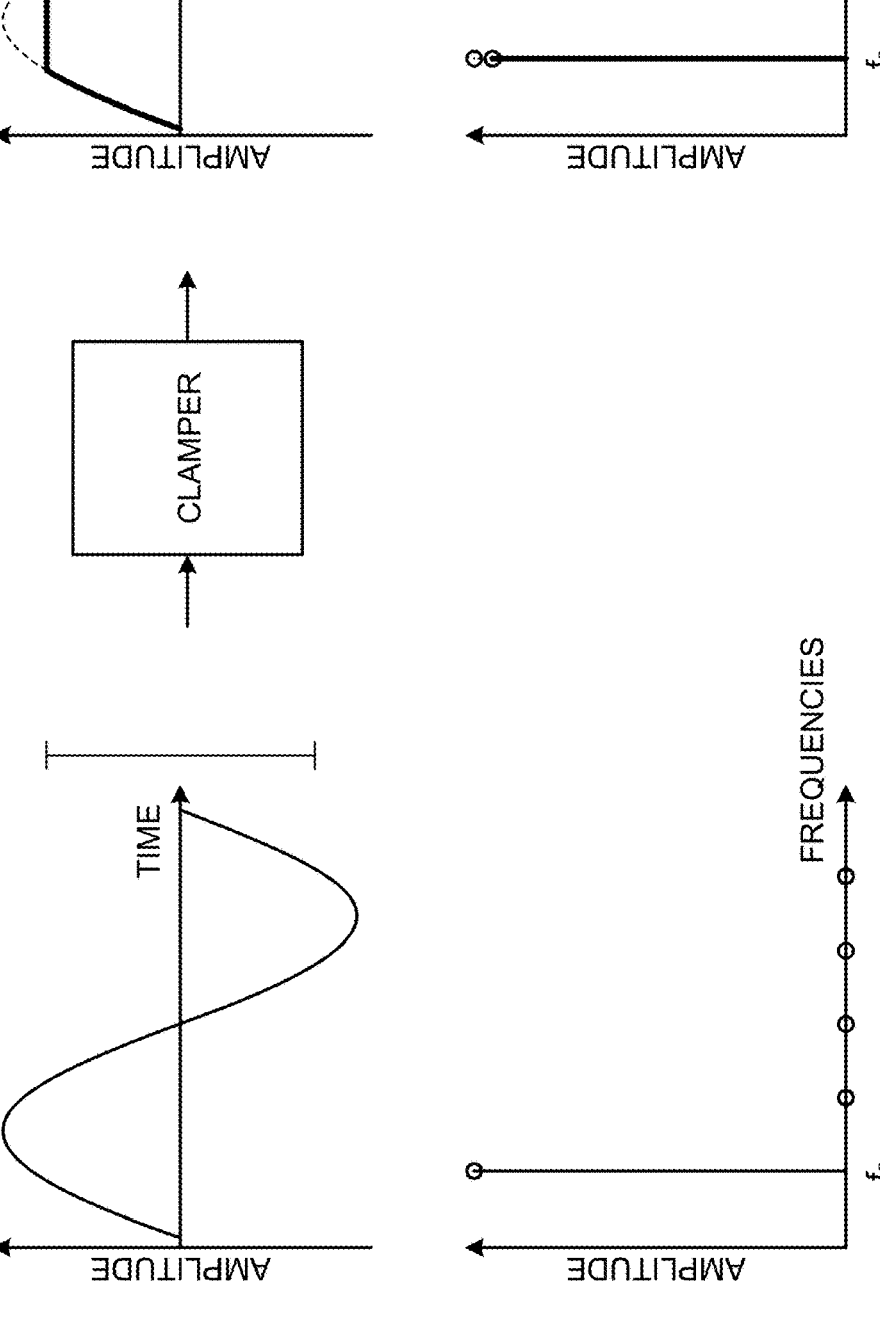

FIGS. 2 and 3 are drawings for explaining an example of the relationship between an operation of the clamping circuitry 102a and the saturation phenomenon. As illustrated in FIG. 2, the clamping circuitry 102a is configured to clip an output of a reflected-wave signal exceeding a signal tolerance range (an excessively large reflected-wave signal) so as to have a prescribed amplitude value. When the reflected-wave signal has been clipped, because the output of the reflected-wave signal is in the state of not reflecting an output intensity in actuality, the saturation phenomenon occurs.

Further, as illustrated on the right-hand side of FIG. 3, when the reflected-wave signal has been clipped, the waveform of the reflected wave has a linear shape in the part exceeding the prescribed amplitude value. In other words, when the reflected-wave signal has been clipped, the waveform of the reflected-wave signal exhibits rectangular shapes. Accordingly, it can be said that clipping the reflected-wave signal is equivalent to convoluting a rectangular wave. The rectangular wave is expressed with overlapping of odd-numbered order components. In other words, when the reflected-wave signal has been clipped, an odd-numbered order harmonic wave occurs.

In relation to the above, the ultrasound diagnosis apparatus 1 according to the present embodiment is configured to use a third harmonic component for the harmonic imaging. However, the odd-numbered order harmonic wave occurring from the clamping process described above includes a third harmonic wave (which hereinafter may be referred to as "saturation impact component"). For this reason, when the saturation impact component occurs, there is a possibility that an ultrasound image impacted by the saturation impact component may be generated. In that situation, the saturation impact component causes excessive contrast in the ultrasound image, which may be a cause of degradation of image quality.

Figure 4:
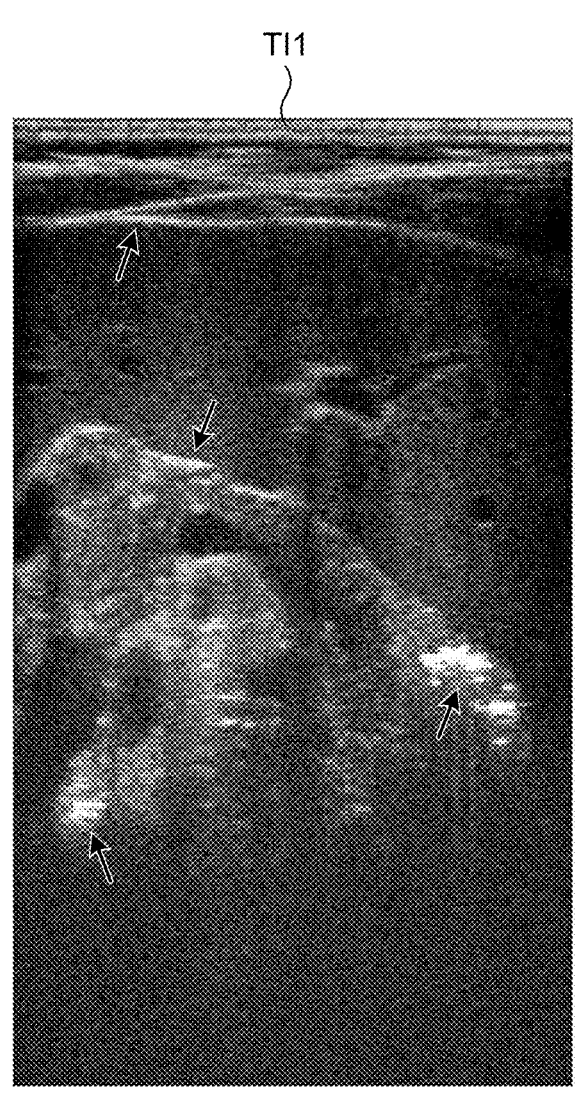
FIG. 4 is a drawing illustrating an example of an ultrasound image generated by implementing a third harmonic imaging method according to the first embodiment.
Figure 4:

Next, FIG. 4 is a drawing illustrating an example of an ultrasound image TI1 generated by implementing a third harmonic imaging method. The arrows in FIG. 4 indicate saturation regions where a third harmonic component derived from reflected-wave data overlaps with the saturation impact component. As illustrated in FIG. 4, because the saturation regions in the ultrasound image TI1 has an extremely large brightness values, there is a possibility that bright regions may exhibit blown-out highlights and may cause excessive contrast. In other words, when an ultrasound image has a saturation region, there is a possibility that the image quality may be degraded.

To cope with the circumstances described above, the ultrasound diagnosis apparatus 1 according to the present embodiment is configured, for the imaging process, to perform a replacement process by which the reflected-wave data including the third harmonic component is replaced with reflected-wave data of a second harmonic wave having no impact from the saturation impact component, for the purpose of suitably reducing the image degradation caused by the saturation impact component. The replacement process performed on the reflected-wave data will be explained later.

Returning to the description of FIG. 1, the buffer memory 103 is configured to at least temporarily store therein the reflected-wave data (the IQ data) generated by the ultrasound reception circuitry 102. For example, the buffer memory 103 is configured to store therein the reflected-wave data corresponding to a number of frames or the reflected-wave data corresponding to a number of volumes. For example, under control of the ultrasound reception circuitry 102, the buffer memory 103 is configured to store therein the reflected-wave data corresponding to a prescribed number of frames.

Further, when reflected-wave data corresponding to another frame is newly generated by the ultrasound reception circuitry 102, while the buffer memory 103 has stored therein the reflected-wave data corresponding to the prescribed number of frames, the buffer memory 103 is configured to discard the reflected-wave data corresponding to the one frame generated earliest and to store therein the reflected-wave data corresponding to the one frame that was newly generated, under control of the ultrasound reception circuitry 102.

For example, the buffer memory 103 is realized by using a semiconductor memory element such as a Random Access Memory (RAM), a flash memory, or the like. The reflected-wave data corresponding to one frame generated by the ultrasound reception circuitry 102 is reflected-wave data corresponding to one acquisition frame. The buffer memory 103 may be referred to as a temporary memory.

The raw data memory 104 is configured to store therein various types of data such as B-mode data and Doppler data generated by the processing circuitry 108 (explained later). The raw data memory 104 is realized by using a semiconductor memory element such as a RAM or a flash memory, or a hard disk, an optical disk, or the like.

For example, the memory 105 is realized by using a magnetic or optical storage medium, a semiconductor memory element such as a flash memory, a hard disk, a storage medium such as an optical disc readable by a processor, or the like. The memory 105 has stored therein a program for realizing the ultrasound wave transmission and reception, various types of data, and the like.

The program and the various types of data may be stored in the memory 105 in advance or may be distributed as being stored in a non-transitory storage medium, for example, so as to be read from the non-transitory storage medium and installed into the memory 105.

The image memory 106 is configured to store therein the various types of image data generated by the processing circuitry 108. For example, the image memory 106 is realized by using a semiconductor memory element such as a RAM or a flash memory, or a hard disk, an optical disk, or the like. In an example, the raw data memory 104 and the image memory 106 may be integrated together as one memory.

The communication interface 107 is connected to the external apparatus 30 via the network NW, for example, and is configured to perform data communication with the external apparatus 30.

For example, the external apparatus 30 is a workstation configured to perform post-processing on various types of data generated by the ultrasound diagnosis apparatus 1 and a process of displaying the ultrasound image data and the like. For example, the external apparatus 30 includes processing circuitry such as a processor, a storage apparatus, and a display. Alternatively, the external apparatus 30 may be a tablet terminal or the like.

The input interface 130 is configured to receive various types of instructions from the operator via the input apparatus 22. The input interface 130 is connected to the processing circuitry 108 via a bus, for example, and is configured to convert an operation instruction input by the operator into an electrical signal and to output the electrical signal to the processing circuitry 108.

In this situation, the input interface 130 does not necessarily have to be connected to physical operation component parts such as a mouse, a keyboard, and/or the like. For instance, possible examples of the input interface include circuitry configured to receive an electrical signal corresponding to an operation instruction input thereto from an external input mechanism provided separately from the ultrasound diagnosis apparatus 1 and to output the electrical signal to the processing circuitry 108.

For example, the output interface 140 is configured to output an electrical signal from the processing circuitry 108 to the outside. The output interface 140 is connected to the processing circuitry 108 via a bus, for example, and is configured to output an electrical signal from the processing circuitry 108 to the display 23.

The processing circuitry 108 is a processor configured to realize functions corresponding to programs by reading and executing programs from the memory 105. The processing circuitry 108 according to the present embodiment includes an extracting function 110, a B-mode processing function 111, a Doppler processing function 112, an image generating function 113, a saturation detecting function 114, a calculating function 115, a display controlling function 116, and a system controlling function 117.

In this situation, for example, constituent elements of the processing circuitry 108, namely, the processing functions such as the extracting function 110, the B-mode processing function 111, the Doppler processing function 112, the image generating function 113, the saturation detecting function 114, the calculating function 115, the display controlling function 116, and the system controlling function 117 are stored in the memory 105 in the form of computer-executable programs.

For example, the processing circuitry 108 is configured to realize the functions corresponding to the programs, by reading and executing the programs from the memory 105. In other words, the processing circuitry 108 that has read the programs has the functions illustrated within the processing circuitry 108 in FIG. 1.

With reference to FIG. 1, the example was explained in which the single processor realizes the processing functions carried out by the extracting function 110, the B-mode processing function 111, the Doppler processing function 112, the image generating function 113, the saturation detecting function 114, the calculating function 115, the display controlling function 116, and the system controlling function 117; however, it is also acceptable to structure the processing circuitry 108, by combining together a plurality of independent processors, so that the functions are realized as a result of the processors executing the programs.

Further, with reference to FIG. 1, the example was explained in which the single memory (i.e., the memory 105) has stored therein the programs corresponding to the processing functions; however, another arrangement is also acceptable in which a plurality of memories are provided in a distributed manner, so that the processing circuitry 108 reads corresponding programs from the individual memories.

In the description above, the example was explained in which the "processor" is configured to read and execute the programs corresponding to the functions, from the memory; however, possible embodiments are not limited to this example. The term "processor" denotes, for example, a Central Processing Unit (CPU), a Graphics Processing Unit (GPU), or circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)).

When the processor is a CPU, for example, the processor is configured to realize the functions by reading and executing the programs saved in the memory 105. In contrast, when the processor is an ASIC, instead of having the programs saved in the memory 105, the functions are directly incorporated into the circuitry of the processor as logic circuitry.

Further, the processors of the present embodiment do not each necessarily have to be structured as a single piece of circuitry. It is also acceptable to structure one processor by combining together a plurality pieces of independent circuitry, so as to realize the functions thereof. Further, it is also acceptable to integrate two or more of the constituent elements illustrated in FIG. 1 into one processor so as to realize the functions thereof.

The extracting function 110 is configured to extract a harmonic component of arbitrary order, by performing a process on a plurality of pieces of reflected-wave data. For example, the extracting function 110 is configured to extract a second harmonic component and a third harmonic component from the plurality of pieces of reflected-wave data. The second harmonic component is an example of the second signal. Further, the third harmonic component is an example of the first signal.

As for a method for extracting the harmonic components, it is possible to adopt any of publicly-known methods (see, for example, the method for extracting a second harmonic wave and a third harmonic wave disclosed in Japanese Patent Application Laid-open No. 2016-112400 or the like).

In an example of extracting the second harmonic component, the ultrasound transmission circuitry 101 is configured to cause the ultrasound probe 21 to perform ultrasound transmission twice (e.g., ultrasound transmission of which the phases correspond to 0 degrees and 180 degrees), by staggering the phases of the transmitted ultrasound waves (the phase of a single center frequency included in each ultrasound wave) by 180 degrees.

In that situation, the ultrasound reception circuitry 102 is configured to generate pieces of reflected-wave data related to a reception scanning line in common, on the basis of two reflected-wave signals obtained from the ultrasound transmission performed twice. Subsequently, the extracting function 110 is configured to extract the second harmonic component by adding together the two pieces of reflected-wave data staggered by 180 degrees.

In this situation, possible methods for extracting the second harmonic wave are not limited to the example described above. For instance, the extracting function 110 may extract a second harmonic component by turning the phase of the reflected-wave data by 0 degrees, 120 degrees, and 240 degrees and subsequently adding the data together.

Further, in an example of extracting the third harmonic component, the ultrasound transmission circuitry 101 is configured to cause the ultrasound probe 21 to perform ultrasound transmission three times (e.g., ultrasound transmission of which the phases correspond to 0 degrees, 120 degrees, and 240 degrees), by staggering the phases of the transmitted ultrasound waves by 120 degrees.

In that situation, the ultrasound reception circuitry 102 is configured to generate pieces of reflected-wave data related to a reception scanning line in common, on the basis of three reflected-wave signals obtained from the ultrasound transmission performed three times. The extracting function 110 is configured to extract the third harmonic component by adding together the three signals staggered by 120 degrees.

In this situation, possible methods for extracting the third harmonic wave are not limited to the example described above. For instance, the extracting function 110 may extract a third harmonic component by performing subtraction on the reflected-wave data corresponding to 0 degrees and 180 degrees and subsequently applying a filter.

The B-mode processing function 111 is configured to generate B-mode data from the reflected-wave data.

For example, the B-mode processing function 111 is configured to generate data (B-mode data) in which signal intensities are expressed with brightness levels, by performing a logarithmic compression process or the like on the harmonic components extracted from the reflected-wave data. The B-mode processing function 111 is configured to store the generated B-mode data into the raw data memory 104, as B-mode raw data on two-dimensional ultrasound scanning lines (raster). Alternatively, the B-mode raw data may be B-mode data on three-dimensional ultrasound wave scanning lines.

Further, the B-mode processing function 111 is configured to correct the third harmonic component of the saturation region, on the basis of the second harmonic component of the saturation region.

For example, when the saturation region is detected, the B-mode processing function 111 is configured to perform a process (which hereinafter may be referred to as "replacement process") of replacing the third harmonic component of the saturation region with a second harmonic component of which the signal intensity has been shifted. The replacement process is an example of a correction. In this situation, the B-mode processing function 111 is configured to generate B-mode data by performing a logarithmic compression process or the like on the third harmonic component resulting from the replacement process.

In this situation, the second harmonic component of which the signal intensity has been shifted is an example of a signal based on the second signal. In another example, the B-mode processing function 111 may simply replace the third harmonic component of the saturation region with the second harmonic component, without performing the process of shifting the signal intensity. In yet another example, it is also acceptable to replace only a part of the third harmonic component of the saturation region, with the second harmonic component.

The Doppler processing function 112 is configured to generate data (Doppler data) obtained by extracting movement information based on the Doppler effect of moving objects present in a Region Of Interest (ROI) set in a scan region, by performing a frequency analysis on the IQ data stored in the buffer memory 103.

For example, the Doppler processing function 112 is capable of implementing a color Doppler method that may be called a Color Flow Mapping (CFM) method. The Doppler processing function 112 is configured to store the generated Doppler data into the raw data memory 104 as Doppler raw data on two-dimensional ultrasound scanning lines. Alternatively, the Doppler raw data may be Doppler data on three-dimensional ultrasound wave scanning lines.

The image generating function 113 is configured to generate B-mode image data on the basis of the B-mode raw data generated by the B-mode processing function 111. Further, the image generating function 113 is configured to generate Doppler image data on the basis of the Doppler raw data generated by the Doppler processing function 112.

For example, the image generating function 113 is configured to generate two-dimensional ultrasound image data structured with pixels, by performing a raw/pixel conversion on the B-mode raw data and the Doppler raw data. The ultrasound image data may be, for example, B-mode image data, color Doppler image data, Doppler waveform image data, or the like.

In another example, the image generating function 113 may generate volume data by performing a raw-voxel conversion including an interpolating process that takes spatial position information into account, on the B-mode raw data stored in the raw data memory.

Further, the image generating function 113 may generate rendering image data or Multi Planar Reconstruction (MPR) image data by performing a rendering process or an MPR process on various types of volume data, for example. The image generating function 113 is configured to store the generated ultrasound image data into the image memory 106.

The saturation detecting function 114 is configured to detect the saturation region. For example, the saturation detecting function 114 is configured to detect, as the saturation region, a region in which signal intensities (brightness values) exceed a predetermined threshold value, from the ultrasound image data (which hereinafter may be referred to as "third harmonic image data") based on the B-mode data generated from the reflected-wave data of the third harmonic component.

Alternatively, the saturation detecting function 114 may be configured to detect the saturation region, by using a trained model generated on the basis of existing machine learning technology (including deep learning).

In that situation, for example, the saturation detecting function 114 is configured to input the third harmonic image data to the trained model provided with a function of receiving an input of third harmonic image data and outputting information indicating a saturation region in the third harmonic image data. Further, the saturation detecting function 114 is configured to detect the saturation region, on the basis of an output result from the trained model.

In this situation, the trained model may be, for example, a trained model that uses a data set made up of third harmonic image data serving as input-side training data and information (e.g., coordinates of the saturation region) indicating the saturation region in the third harmonic image data serving as output-side training data, so as to learn a relationship between the two. In that situation, the trained model is stored in a storage apparatus of the external apparatus 30 or the like, for example.

When the saturation region has been detected, the calculating function 115 is configured to calculate, on the basis of a statistical value, a signal value offset for inhibiting excessive contrast in the ultrasound image, with respect to the second harmonic component to be used in the replacement process. For example, the calculating function 115 is configured to generate histograms of the signal intensities (the brightness values) with respect to the second harmonic image data and the third harmonic image data.

Further, the calculating function 115 is configured to compare the two histograms with each other and to calculate a shift amount for an average value of signal intensities (brightness values) of the pixels in the second harmonic image data that is necessary in order to match the average value of the signal intensities (the brightness values) of the pixels in the second harmonic image data with an average value of signal intensities (brightness values) of the pixels in the third harmonic data.

Subsequently, the B-mode processing function 111 is configured to replace a signal corresponding to the saturation region in the third harmonic image data with a signal corresponding to a region equivalent to the saturation region in the second harmonic component, to which the shift amount for the average value of the signal intensities (the brightness values) calculated by the calculating function 115 is applied as the signal value offset. Although the signal value offset is calculated by using the average value as the statistical value in the above example, it is also acceptable, for example, to calculate a signal value offset by using a statistical value other than the average value, such as a median.

Further, although the signal value offset is calculated by using the simply-calculated average value in the above example, the calculating function 115 may be configured to calculate a signal value offset by using a statistical value calculated by further taking a standard deviation or the like into account. For example, it is acceptable to calculate a signal value offset by using an average value calculated from only the values in the range from −2SD to +2SD where SD denotes a standard deviation.

Next, a reason why the replacement process is performed after applying the signal value offset based on the statistical value as described above will be explained. First of all, generally speaking, an average value of signal intensities (brightness values) of the pixels in ultrasound image data (which hereinafter may be referred to as "second harmonic image data") based on B-mode data generated from reflected-wave data of a second harmonic component is larger than an average value of signal intensities (brightness values) of the pixels in third harmonic image data. In other words, generally speaking, second harmonic images have larger brightness values as a whole than third harmonic images.

Further, the region in a second harmonic image corresponding to a saturation region in a third harmonic image tends to have large brightness values in many situations. For this reason, for a saturation region, if a third harmonic component were simply replaced with a second harmonic component, because the pixels in the saturation region would be replaced with the pixels having large brightness values, it might not be possible, in some situation, to sufficiently inhibit excessive contrast.

To cope with this problem, with respect to the saturation region, by replacing the third harmonic component with the second harmonic component after applying the signal value offset based on the statistical value, it is possible to lower the brightness values of the replacing pixels, and it is therefore possible to inhibit excessive contrast better than when the simple replacement is performed.

Although the B-mode processing function 111 is configured to perform the replacement process in the above example, the image generating function 113 may be configured to perform a process corresponding to the replacement process. For example, the image generating function 113 may be configured to generate ultrasound image data obtained by replacing the pixels corresponding to the saturation region in the third harmonic image data with the post-shift pixels in a region corresponding to the saturation region in the second harmonic image data.

The display controlling function 116 is configured to cause the display 23 to display ultrasound images based on various types of ultrasound image data generated by the image generating function 113.

For example, the display controlling function 116 is configured to cause the display 23 to display an ultrasound image based on ultrasound image data (which hereinafter may be referred to as "saturation countermeasure processed image data") generated from the B-mode data based on the third harmonic component resulting from the replacement process. Further, the display controlling function 116 may cause the display 23 to display a GUI used by the operator for inputting the various types of setting requests via the input apparatus 22.

The system controlling function 117 is configured to integrally control operations of the entirety of the ultrasound diagnosis apparatus 1. For example, the system controlling function 117 is configured to control an ultrasound scan, by controlling the ultrasound probe 21 via the ultrasound transmission circuitry 101.

Figure 5:
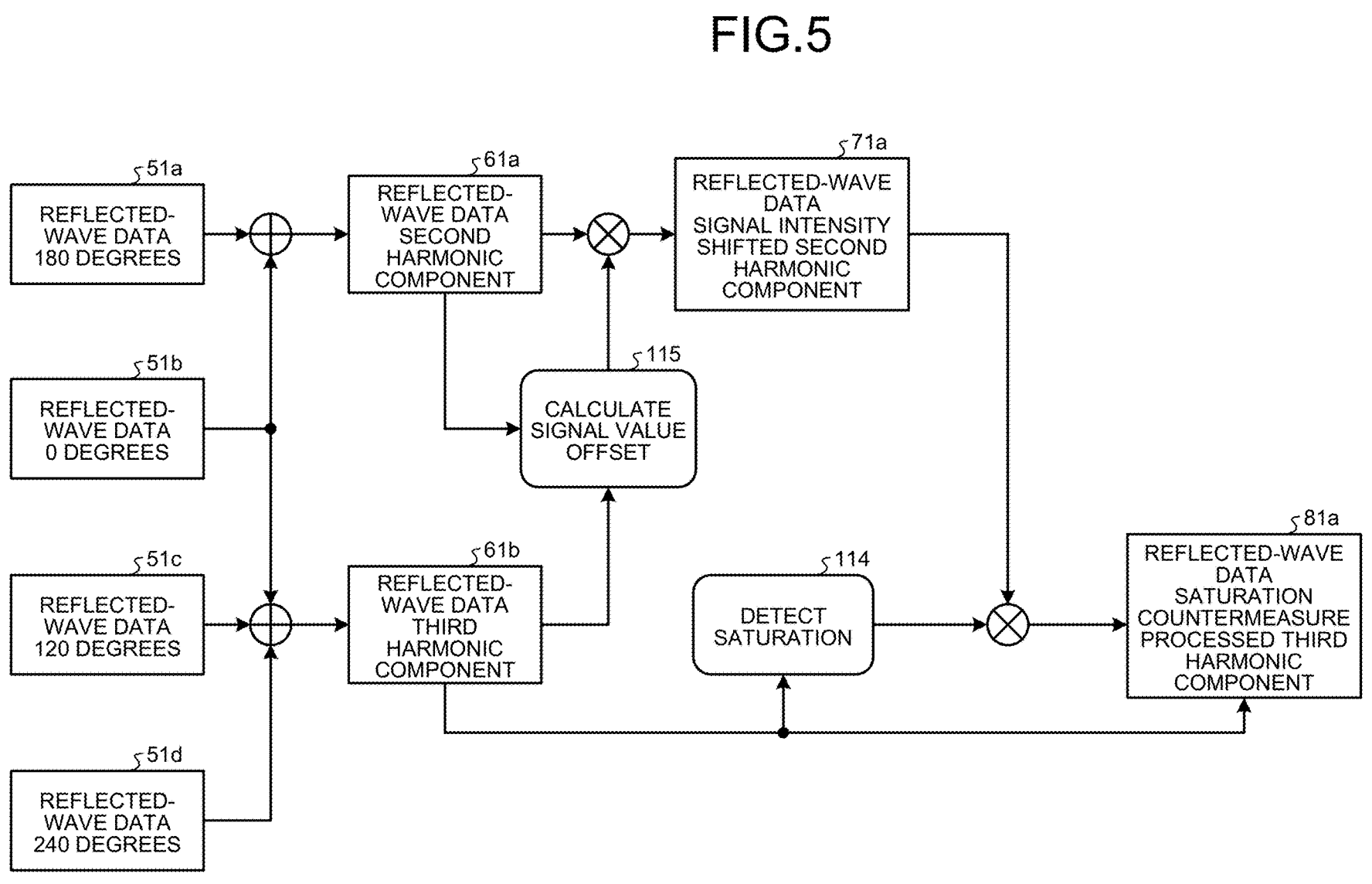

Next, a flow of processes including the replacement process according to the first embodiment will be explained, with reference to FIGS. 5 to 7. FIG. 5 is a chart for explaining an example of the flow of the processes including the replacement process.

In FIG. 5, reflected-wave data (180 degrees) 51a is reflected-wave data generated on the basis of a reflected-wave signal of an ultrasound wave transmitted while the phase is set to 180 degrees. Also, reflected-wave data (0 degrees) 51b is reflected-wave data generated on the basis of a reflected-wave signal of an ultrasound wave transmitted while the phase is set to 0 degrees.

Further, reflected-wave data (120 degrees) 51c is reflected-wave data generated on the basis of a reflected-wave signal of an ultrasound wave transmitted while the phase is set to 120 degrees. Also, reflected-wave data (240 degrees) 51d is reflected-wave data generated on the basis of a reflected-wave signal of an ultrasound wave transmitted while the phase is set to 240 degrees.

The extracting function 110 generates reflected-wave data (second harmonic component) 61a by adding together the reflected-wave data (180 degrees) 51a and the reflected-wave data (0 degrees) 51b. Similarly, the extracting function 110 generates reflected-wave data (third harmonic component) 61b by adding together the reflected-wave data (0 degrees) 51b, the reflected-wave data (120 degrees) 51c, and the reflected-wave data (240 degrees) 51d.

The B-mode processing function 111 generates B-mode data based on the reflected-wave data (the second harmonic component) 61a, by performing a logarithmic compression process or the like on the reflected-wave data (the second harmonic component) 61a. Similarly, the B-mode processing function 111 generates B-mode data based on the reflected-wave data (the third harmonic component) 61b, by performing a logarithmic compression process or the like on the reflected-wave data (the third harmonic component) 61*b*.

The image generating function 113 generates second harmonic image data from the B-mode data based on the reflected-wave data (the second harmonic component) 61*a*. Similarly, the image generating function 113 generates third harmonic image data from the B-mode data based on the reflected-wave data (the third harmonic component) 61*b*.

Further, the saturation detecting function 114 detects, as a saturation region, a region having pixels exhibiting brightness values exceeding a threshold value, from the third harmonic image data generated by the image generating function 113.

When the saturation region has been detected, the calculating function 115 generates histograms of the signal intensities (the brightness values) with respect to the reflected-wave data (the second harmonic component) 61*a* and the reflected-wave data (the third harmonic component) 61*b*. The calculating function 115 calculates a signal value offset, on the basis of the generated histograms of the signal intensities (the brightness values) of the two, an average value of the signal intensities (the brightness values) of the reflected-wave data (the second harmonic component) 61*a*, and an average value of the signal intensities (the brightness values) of the reflected-wave data (the third harmonic component) 61*b*.

Figure 6:
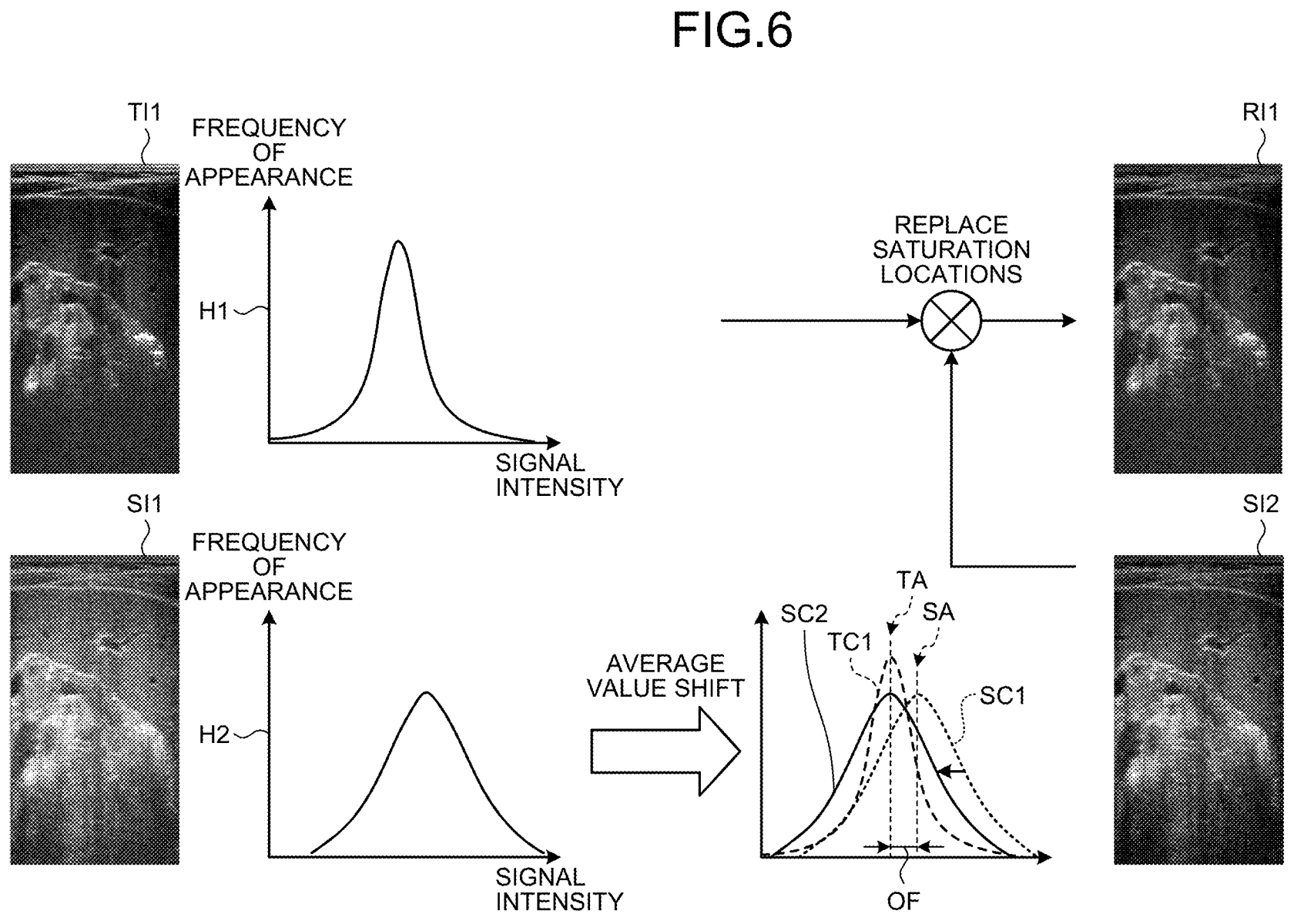

Next, FIG. 6 is a drawing for explaining an example of processes including the signal value offset calculating process. The third harmonic image TI1 illustrated in FIG. 6 is an ultrasound image based on the third harmonic image data generated on the basis of the reflected-wave data (the third harmonic component) 61*b*. As illustrated in FIG. 4, the third harmonic image TI1 has excessive contrast occurring in the saturation region.

In the following sections, data of the third harmonic image TI1 generated on the basis of the reflected-wave data (the third harmonic component) 61*b* may be referred to as third harmonic image data TI1.

Further, a second harmonic image SI1 is an ultrasound image based on second harmonic image data generated on the basis of the reflected-wave data (the second harmonic component) 61*a*. As explained above, the second harmonic image SI1 is a whitish image having large brightness values as a whole. Further, in the second harmonic image SI1, the region corresponding to the saturation region in the third harmonic image TI1 has particularly large brightness values.

In the following sections, data of the second harmonic image SI1 generated on the basis of the reflected-wave data (the second harmonic component) 61*a* may be referred to as second harmonic image data SI1.

The calculating function 115 obtains the signal intensities (the brightness values) of the images structuring the third harmonic image data TI1. On the basis of the obtained signal intensities (brightness values) of the images, the calculating function 115 generates a histogram H1 of the third harmonic image data TI1, by expressing frequency of appearance on the vertical axis and the signal intensities (the brightness values) on the horizontal axis.

Further, the calculating function 115 similarly obtains the signal intensities (the brightness values) of the images structuring the second harmonic image data SI1. On the basis of the obtained signal intensities (brightness values) of the images, the calculating function 115 generates a histogram H2 of the second harmonic image data SI1, by expressing frequency of appearance on the vertical axis and the signal intensities (the brightness values) on the horizontal axis.

The calculating function 115 calculates an average value TA of the signal intensities (the brightness values) of the images structuring the third harmonic image data TI1. Further, the calculating function 115 calculates an average value SA of the signal intensities (the brightness values) of the images structuring the second harmonic image data SI1. Further, the calculating function 115 calculates, as a signal value offset OF, a shift amount for the average value of a second harmonic component SC (i.e., the difference between the average value SA and the average value TA) required to match the average value TA of a third harmonic component TC1 with the average value SA of the second harmonic component SC.

On the basis of a second harmonic component SC2 obtained by shifting the signal intensities, the B-mode processing function 111 generates reflected-wave data (a signal intensity shifted second harmonic component) 71*a* obtained by applying the signal value offset OF calculated by the calculating function 115 to the reflected-wave data (the second harmonic component) 61*a*.

A signal intensity shifted second harmonic image SI2 illustrated in FIG. 6 is an ultrasound image based on the reflected-wave data (the signal intensity shifted second harmonic component) 71*a*. As compared with the second harmonic image SI1, the signal intensity shifted second harmonic image SI2 is an image having smaller brightness values as a whole. Further, in the signal intensity shifted second harmonic image SI2, the brightness values in the region corresponding to the saturation region in the third harmonic image TI1 are also smaller than those in the second harmonic image SI1.

Further, the B-mode processing function 111 generates reflected-wave data (saturation countermeasure processed third harmonic component) 81*a*, by replacing a signal corresponding to the saturation region in the reflected-wave data (the third harmonic component) 61*b*, with a signal of the reflected-wave data (signal intensity shifted second harmonic component) 71*a*.

Further, the B-mode processing function 111 generates B-mode data based on the reflected-wave data (the saturation countermeasure processed third harmonic component) 81*a* by performing a logarithmic compression process or the like on the reflected-wave data (the saturation countermeasure processed third harmonic component) 81*a*. The image generating function 113 generates saturation countermeasure processed third harmonic image data based on the reflected-wave data (the saturation countermeasure processed third harmonic component) 81*a*.

Figure 7:
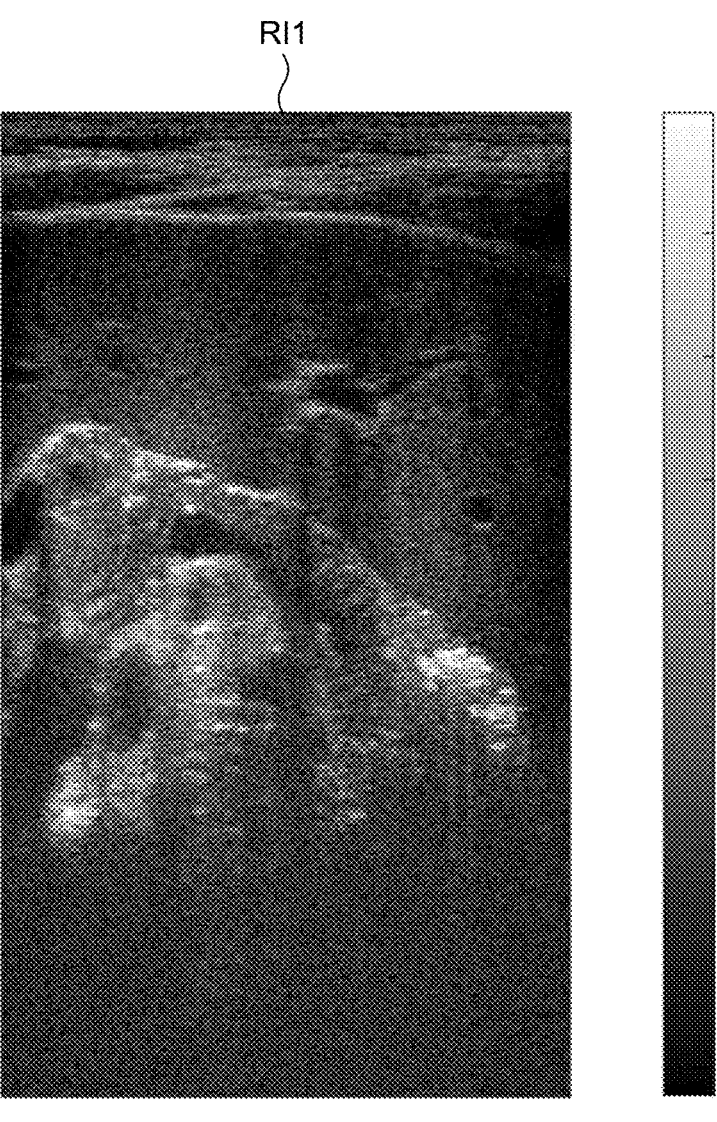
FIG. 7 is a drawing illustrating an example of a saturation countermeasure processed third harmonic image according to the first embodiment.

Next, FIG. 7 is a drawing illustrating an example of a saturation countermeasure processed third harmonic image RI1. As illustrated in FIG. 7, in the saturation countermeasure processed third harmonic image RI1, the brightness values in the saturation region are kept smaller while excessive contrast is inhibited, in comparison to the third harmonic image TI1. In other words, it can be said that the saturation countermeasure processed third harmonic image RI1 has enhanced image quality as compared to the third harmonic image TI1.

In addition to the processes of the functions described above, the processing circuitry 108 may be configured to perform a part or all of the abovementioned processes performed by the clamping circuitry 102*a*.

Figure 8:
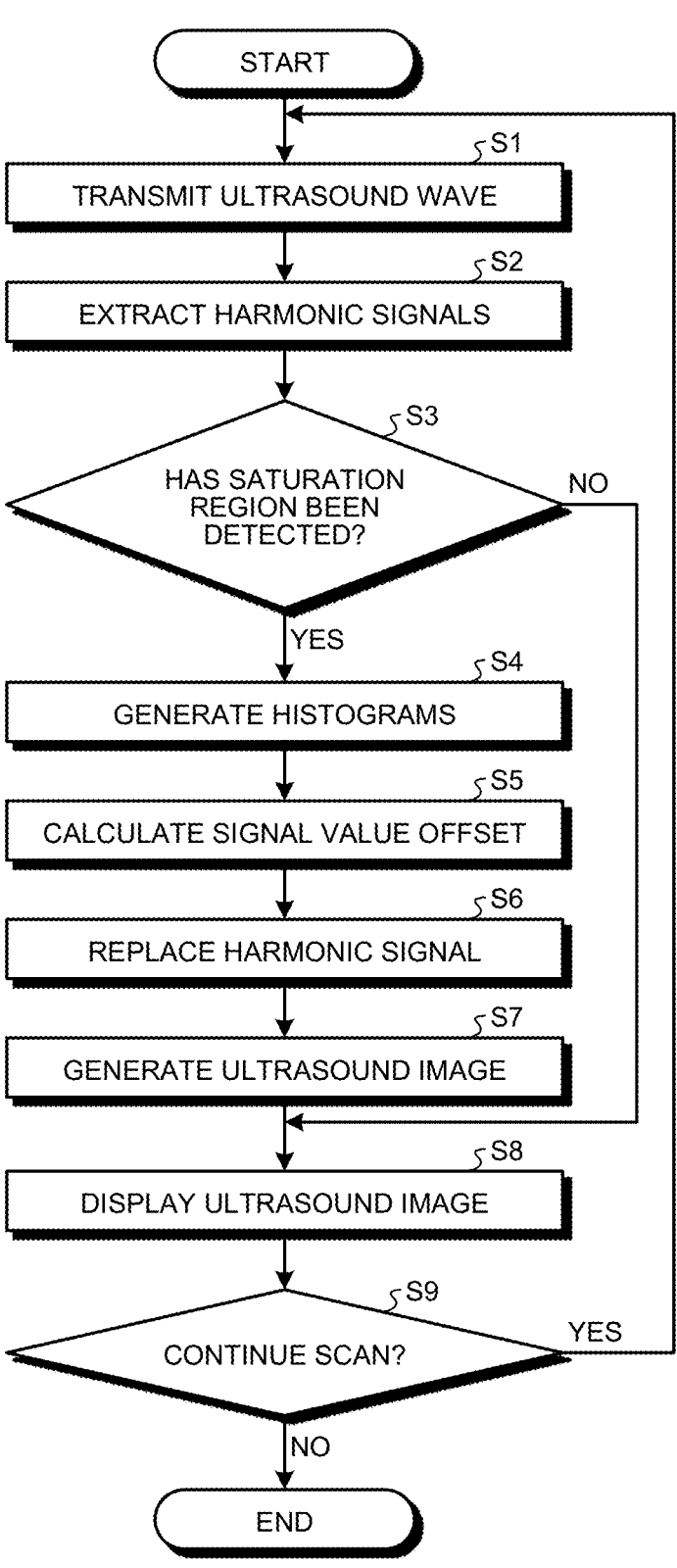
FIG. 8 is a flowchart illustrating an example of processes performed by the ultrasound diagnosis apparatus according to the first embodiment.

Next, processes performed by the ultrasound diagnosis apparatus 1 according to the present embodiment will be explained. FIG. 8 is a flowchart illustrating an example of the processes performed by the ultrasound diagnosis apparatus 1 according to the present embodiment.

To begin with, the system controlling function 117 controls the ultrasound transmission circuitry 101 so as to cause the ultrasound probe 21 to transmit an ultrasound wave multiple times (step S1). For example, the system controlling function 117 causes the ultrasound transmission circuitry 101 to transmit the ultrasound waves while the phases are set to 0 degrees, 120 degrees, 180 degrees, and 240 degrees. The ultrasound reception circuitry 102 receives, as reflected-wave signals, reflected waves of the ultrasound waves transmitted while the phases were set to 0 degrees, 120 degrees, 180 degrees, and 240 degrees and further generates reflected-wave data of each of the received signals.

Subsequently, the extracting function 110 extracts a plurality of harmonic signals from the plurality of pieces of reflected-wave data (step S2). For example, the extracting function 110 extracts a second harmonic component by adding together the reflected-wave data based on the ultrasound wave transmitted while the phase was set to 0 degrees and the reflected-wave data based on the ultrasound wave transmitted while the phase was set to 180 degrees.

Further, for example, the extracting function 110 extracts a third harmonic component by adding together the reflected-wave data based on the ultrasound wave transmitted while the phase was set to 0 degrees, the reflected-wave data based on the ultrasound wave transmitted while the phase was set to 120 degrees, and the reflected-wave data based on the ultrasound wave transmitted while the phase was set to 240 degrees.

After that, the B-mode processing function 111 generates B-mode data based on the second harmonic component and the third harmonic component, by performing a logarithmic compression process or the like on the second harmonic component and the third harmonic component extracted at step S2. Further, the image generating function 113 generates second harmonic image data and third harmonic image data, from the B-mode data based on the second harmonic component and on the third harmonic component.

Subsequently, the saturation detecting function 114 performs the process of detecting a saturation region from the third harmonic image data and checks to see whether a saturation region is present (step S3). For example, the saturation detecting function 114 detects, as the saturation region, pixels exhibiting signal intensities (brightness values) exceeding the threshold value, from the third harmonic image data.

When no saturation region was detected (step S3: No), the process returns to step S8. On the contrary, when a saturation region was detected (step S3: Yes), the calculating function 115 generates histograms of the signal intensities (the brightness values) of the second harmonic image data and the third harmonic image data (step S4).

After that, the calculating function 115 calculates a signal value offset (step S5). For example, the calculating function 115 compares the histogram of the second harmonic image data with the histogram of the third harmonic image data. Further, as the signal value offset, the calculating function 115 calculates a shift amount for the average value of the signal intensities (the brightness values) of the pixels in the second harmonic image data that is required to match the average value of the signal intensities (the brightness values) of the pixels in the second harmonic image data, with the average value of the signal intensities (the brightness values) of the pixels in the third harmonic image data.

Subsequently, the B-mode processing function 111 performs the replacement process on the signals corresponding to the saturation region (step S6). For example, the B-mode processing function 111 replaces the signal corresponding to the saturation region in the reflected-wave data of the third harmonic component with the signal obtained by applying the signal value offset calculated at step S5 to the reflected-wave data of the second harmonic component. After that, the B-mode processing function 111 generates B-mode data by performing a logarithmic compression process or the like on the reflected-wave data of the third harmonic component resulting from the replacement process.

After that, the image generating function 113 generates saturation countermeasure processed ultrasound image data (step S7). For example, the image generating function 113 generates saturation countermeasure processed image data from the B-mode data generated on the basis of the reflected-wave data of the third harmonic component resulting from the replacement process at step S6.

Subsequently, the display controlling function 116 causes an ultrasound image to be displayed (step S8). For example, the display controlling function 116 exercises control so as to cause the display 23 to display the third harmonic image data generated by the image generating function 113 as the ultrasound image.

After that, the system controlling function 117 judges whether or not the scan is to be continued (step S9). For example, when the situation remains for a period of time exceeding a prescribed length where no input is received from the user instructing ultrasound transmission, the system controlling function 117 determines that the scan will not be continued. When it is determined that the scan will be continued (step S9: Yes), the process will return to step S1. On the contrary, when it is determined that the scan will not be continued (step S9: No), the present process is ended.

As explained above, the ultrasound diagnosis apparatus 1 according to the present embodiment is configured to detect the saturation region occurring from the clamping process and is configured, upon detection of the saturation region, to generate the third harmonic component obtained by replacing the reflected-wave data of the third harmonic component with the reflected-wave data of the second harmonic component, with respect to the saturation region.

In this situation, due to the odd-numbered order harmonic wave caused by the saturation phenomenon occurring from the clamping process, excessive contrast could occur, and the image quality of the third harmonic image data could be degraded; however, the second harmonic image data is able to cancel the impact of the odd-numbered order harmonic wave. Accordingly, by replacing the reflected-wave data of the third harmonic component with the reflected-wave data of the second harmonic component with respect to the saturation region, it is possible to prevent the image quality of the third harmonic image from being degraded.

Further, the ultrasound diagnosis apparatus 1 according to the present embodiment is configured to generate the third harmonic component by replacing the reflected-wave data of the third harmonic component with the reflected-wave data of the second harmonic component with respect to the saturation region, after applying, as the signal value offset, the shift amount for the average value of the signal intensities (the brightness values) of the pixels in the second harmonic image data, to the reflected-wave data of the second harmonic component.

Generally speaking, second harmonic image data has higher signal intensities as a whole, in comparison to third harmonic image data. Also, in second harmonic image data, a region corresponding to a saturation region in third harmonic image data tends to have high signal intensities in many situations. Accordingly, by performing the replacement process after applying, as the signal value offset, the shift amount for the average value of the signal intensities (the brightness values) of the pixels in the second harmonic image data, it is possible to more suitably inhibit the occurrence of excessive contrast.

Second Embodiment

In the first embodiment, the example was explained in which the processes such as the replacement process were performed on the reflected-wave data of the third harmonic component. In a second embodiment, processes such as the replacement process are performed on reflected-wave data in which a second harmonic component is blended with a third harmonic component.

Further, in the following sections, differences from the embodiment described above will primarily be explained. Detailed explanations of some of the features that are the same as those previously explained will be omitted. Further, the embodiments described below may be carried out individually or may be carried out in combination as appropriate.

Figure 9:
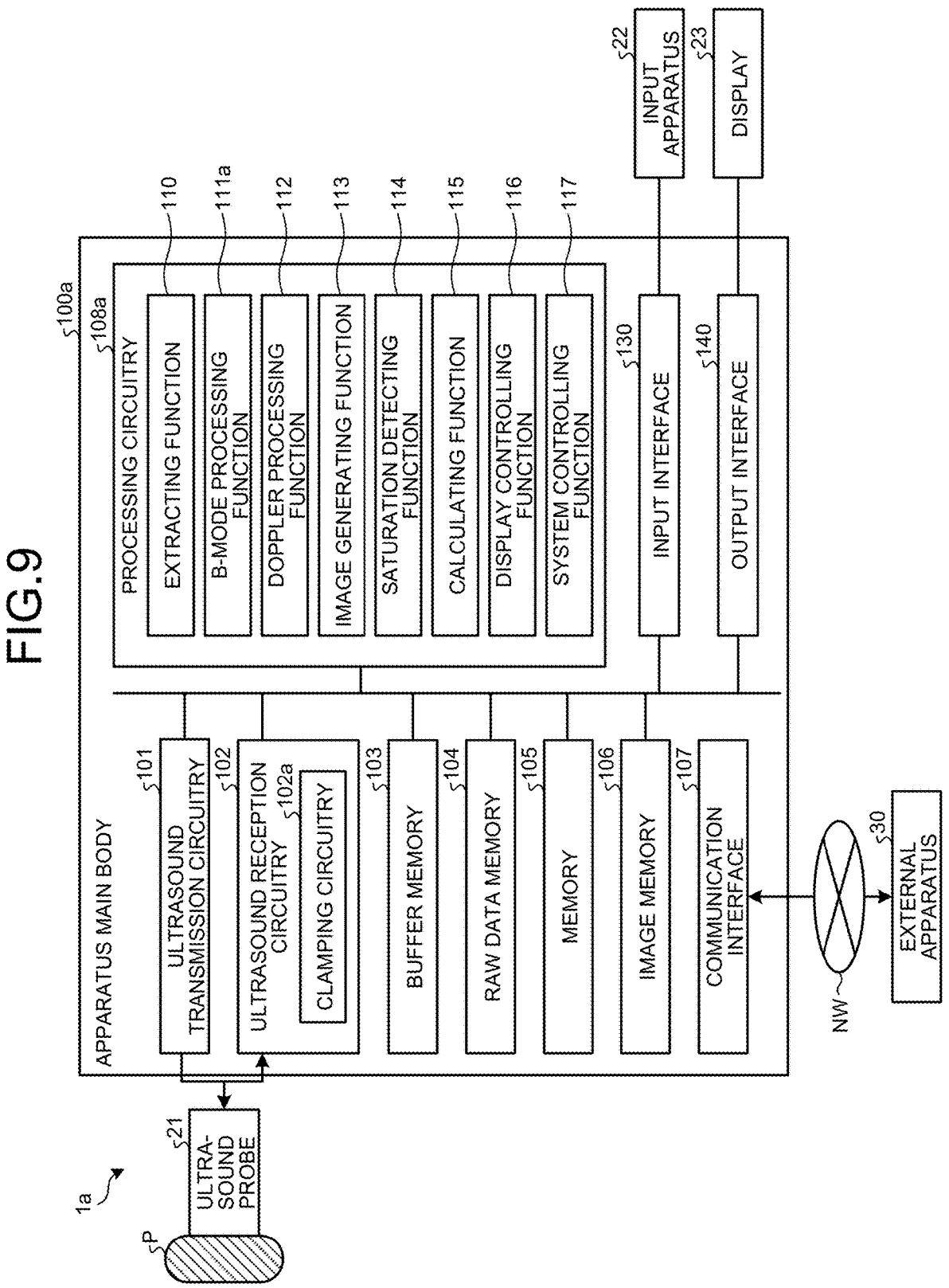
FIG. 9 is a block diagram illustrating an exemplary configuration of an ultrasound diagnosis apparatus according to a second embodiment.

FIG. 9 is a block diagram illustrating an exemplary configuration of an ultrasound diagnosis apparatus 1a according to a second embodiment. The ultrasound diagnosis apparatus 1a according to the present embodiment includes an apparatus main body 100a. The apparatus main body 100a includes processing circuitry 108a. The processing circuitry 108a includes the extracting function 110, a B-mode processing function 111a, the Doppler processing function 112, the image generating function 113, the saturation detecting function 114, the calculating function 115, the display controlling function 116, the system controlling function 117, and a blending function 118.

Because the extracting function 110, the Doppler processing function 112, the image generating function 113, the saturation detecting function 114, the calculating function 115, the display controlling function 116, and the system controlling function 117 will be the same as those in the first embodiment, explanations thereof will be omitted.

To begin with, the blending function 118 will be explained. The blending function 118 is configured to generate blended reflected-wave data obtained by blending together harmonic components of mutually-different order. For example, the blending function 118 is configured to blend a second harmonic component with a third harmonic component, on the basis of respective weights corresponding to distances (which hereinafter may be referred to as "depth") from the ultrasound probe 21.

In this situation, because the third harmonic component has higher directionality (is less impacted by sidelobes) than the second harmonic component, using the third harmonic component is able to achieve higher image quality (resolution) than using the second harmonic component. In addition, when the depth is larger, because the third harmonic component travels a longer distance than when the depth is smaller, the reflected-wave intensities attenuate. Further, the degree of the attenuation of the third harmonic component is more serious than that of the second harmonic component.

To cope with the circumstances described above, the blending function 118 is configured to perform the blending process, by applying a larger weight to the third harmonic component when the depth is smaller and applying a smaller weight to the second harmonic component when the depth is larger. With these arrangements, it is possible to generate an ultrasound image having high image quality, while compensating low depth sensitivity of the third harmonic component.

However, because blended reflected-wave data includes the third harmonic component, when the clamping process is performed, blended image data generated on the basis of the blended reflected-wave data would also experience image quality degradation, similarly to the third harmonic image data.

Figure 10:
FIG. 10 is a drawing illustrating an example of an ultrasound image generated on the basis of blended reflection data according to the second embodiment.
Figure 10:

Next, FIG. 10 is a drawing illustrating an example of an ultrasound image generated on the basis of blended reflection data according to the second embodiment. As indicated by the arrows in FIG. 10, blended reflected-wave data B11 also has excessive contrast occurring in the saturation region. Accordingly, in the present embodiment, the same replacement process as that in the first embodiment is performed on the blended reflected-wave data.

Next, the B-mode processing function 111a will be explained. The B-mode processing function 111a is configured to replace a signal corresponding to the saturation region in the blended image data, with a signal corresponding to the saturation region in the reflected-wave data of the second harmonic component to which the shift amount for the average value of the signal intensities calculated by the calculating function 115 is applied as a signal value offset.

Figure 11:
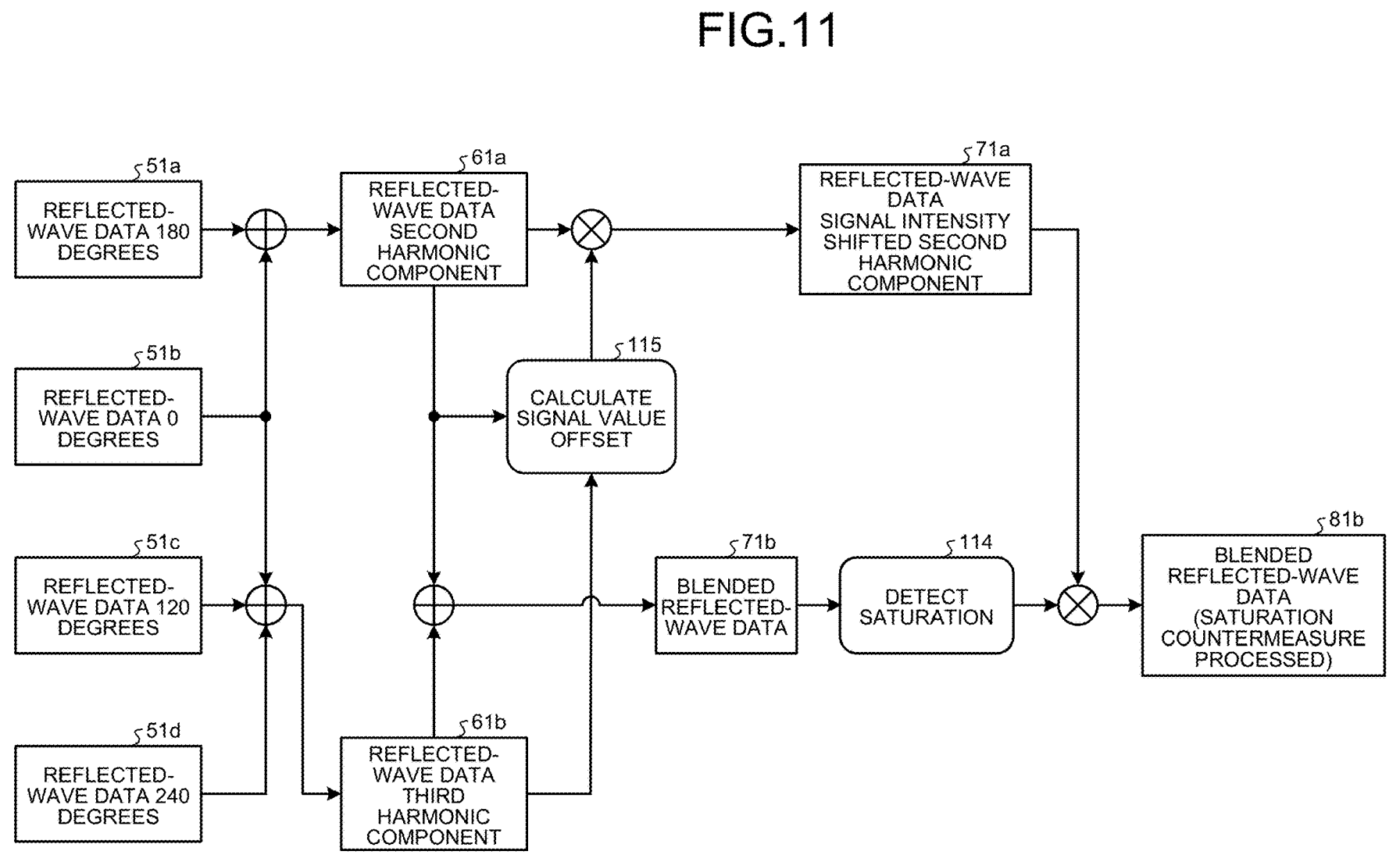

In the following sections, a flow of processes including the blending process according to the second embodiment will be explained, with reference to FIGS. 11 to 13. FIG. 11 is a drawing for explaining an example of the flow of the processes including the blending process. Explanations of some of the processes that are the same as those in FIG. 5 will be omitted.

The blending function 118 generates blended reflected-wave data 71b, by blending the reflected-wave data (the second harmonic component) 61a with the reflected-wave data (the third harmonic component) 61b.

Figure 12:
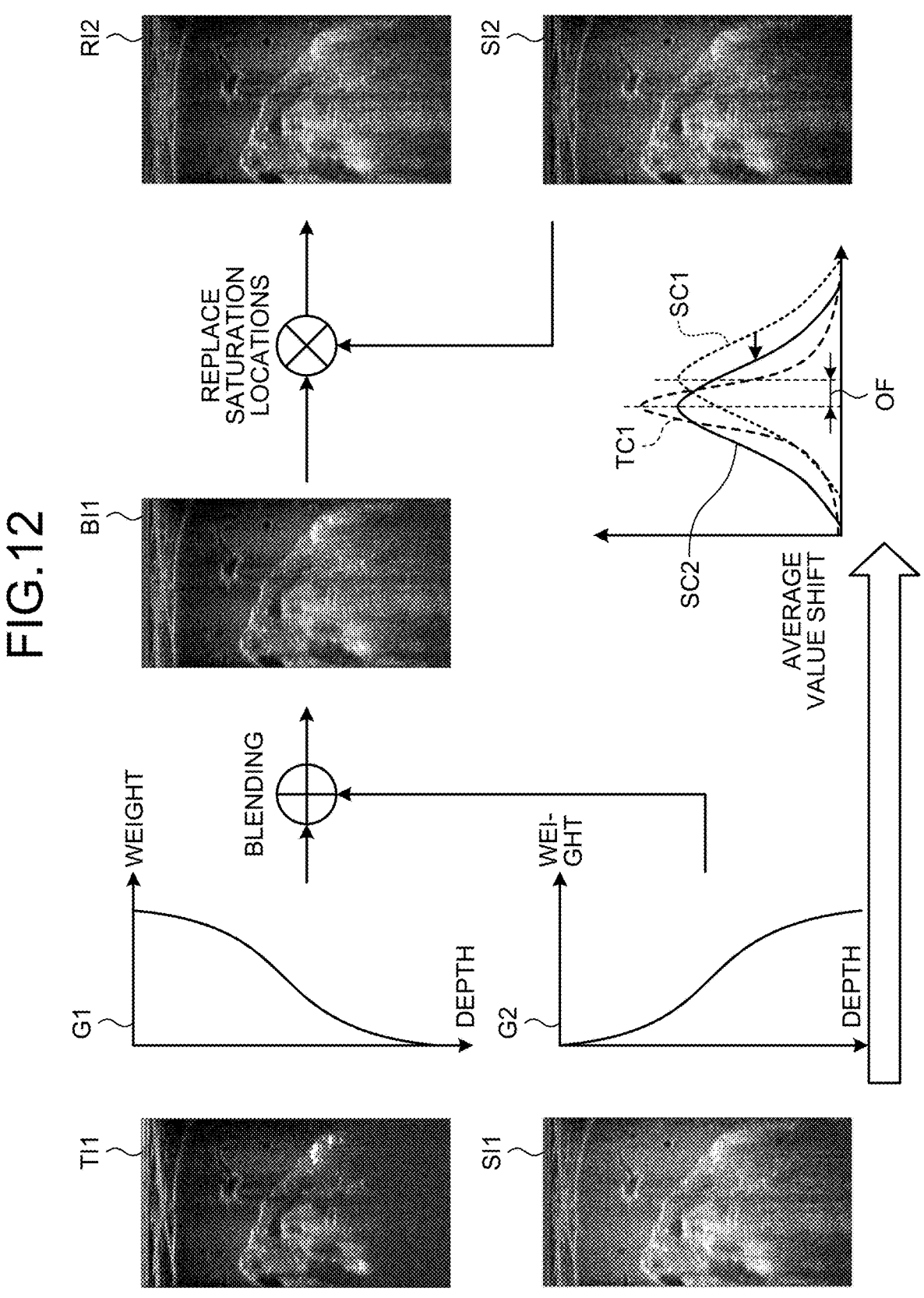
FIG. 12 is a drawing for explaining an example of the processes including the blending process according to the second embodiment.

In relation to the above, FIG. 12 is a drawing for explaining an example of the processes including the blending process. A graph G1 illustrated in FIG. 12 is a graph expressing weights on the third harmonic component as a mathematical function of the depth. Further, a graph G2 is a graph expressing weights on the second harmonic component as a mathematical function of the depth. The blending function 118 refers to the graphs G1 and G2, specifies a weight on the third harmonic component and a weight on the second harmonic component in accordance with the depths, and determines a blending ratio between the third harmonic component and the second harmonic component.

The blending function 118 generates the blended reflected-wave data 71b, by blending the third harmonic component with the second harmonic component in accordance with the determined blending ratio. The B-mode processing function 111a generates B-mode data on the basis of the blended reflected-wave data 71b. The image generating function 113 generates blended image data on the basis of the B-mode data. As illustrated in FIG. 10, a blended image BI1 has excessive contrast occurring in the saturation region.

The B-mode processing function 111a generates blended reflected-wave data (saturation countermeasure processed) 81b, by replacing a signal corresponding to the saturation region in the blended reflected-wave data 71b, with the signal of the reflected-wave data (the signal intensity shifted second harmonic component) 71a.

Further, the B-mode processing function 111a generates B-mode data based on the blended reflected-wave data (saturation countermeasure processed) 81b, by performing a logarithmic compression process or the like on the blended reflected-wave data (saturation countermeasure processed) 81*b*. The image generating function 113 generates saturation countermeasure processed blended image data based on the blended reflected-wave data (saturation countermeasure processed) 81*b*.

Figure 13:
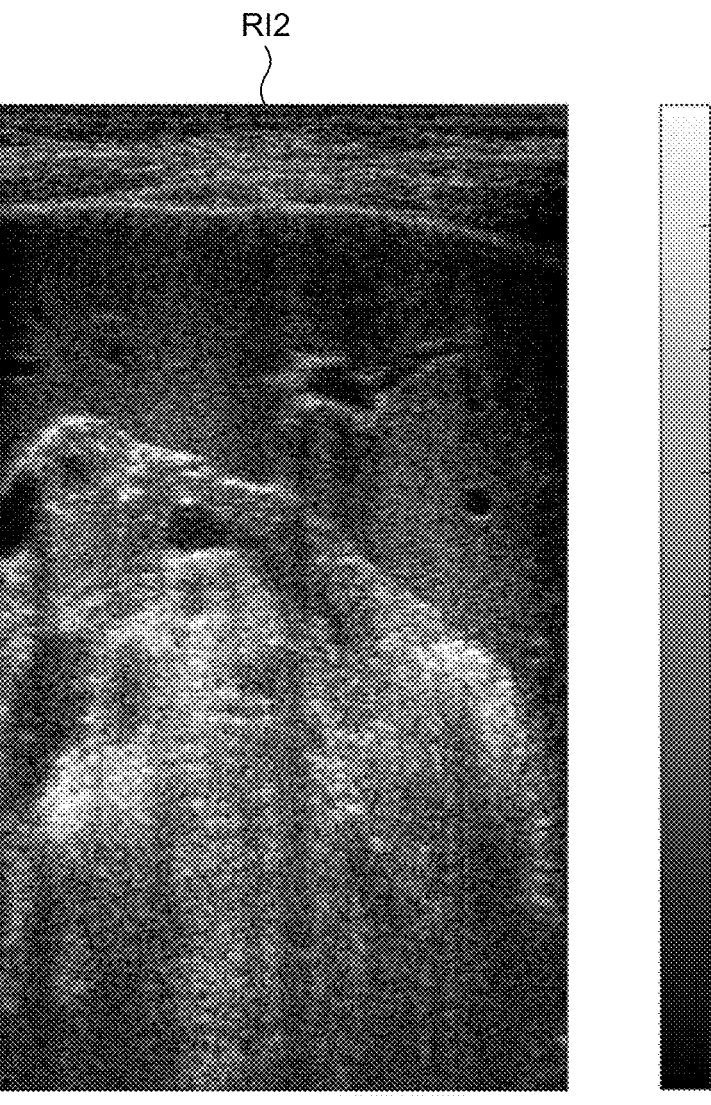
FIG. 13 is a drawing illustrating an example of a saturation countermeasure processed blended ultrasound image according to the second embodiment.

Next, FIG. 13 is a drawing illustrating an example of a saturation countermeasure processed blended image RI2. As illustrated in FIG. 13, in the saturation countermeasure processed blended image RI2, the brightness values in the saturation region are kept small while excessive contrast is inhibited, in comparison to the blended image BI1. In other words, it can be said that the saturation countermeasure processed blended image RI2 has enhanced image quality as compared to the blended image BI1.

Figure 14:
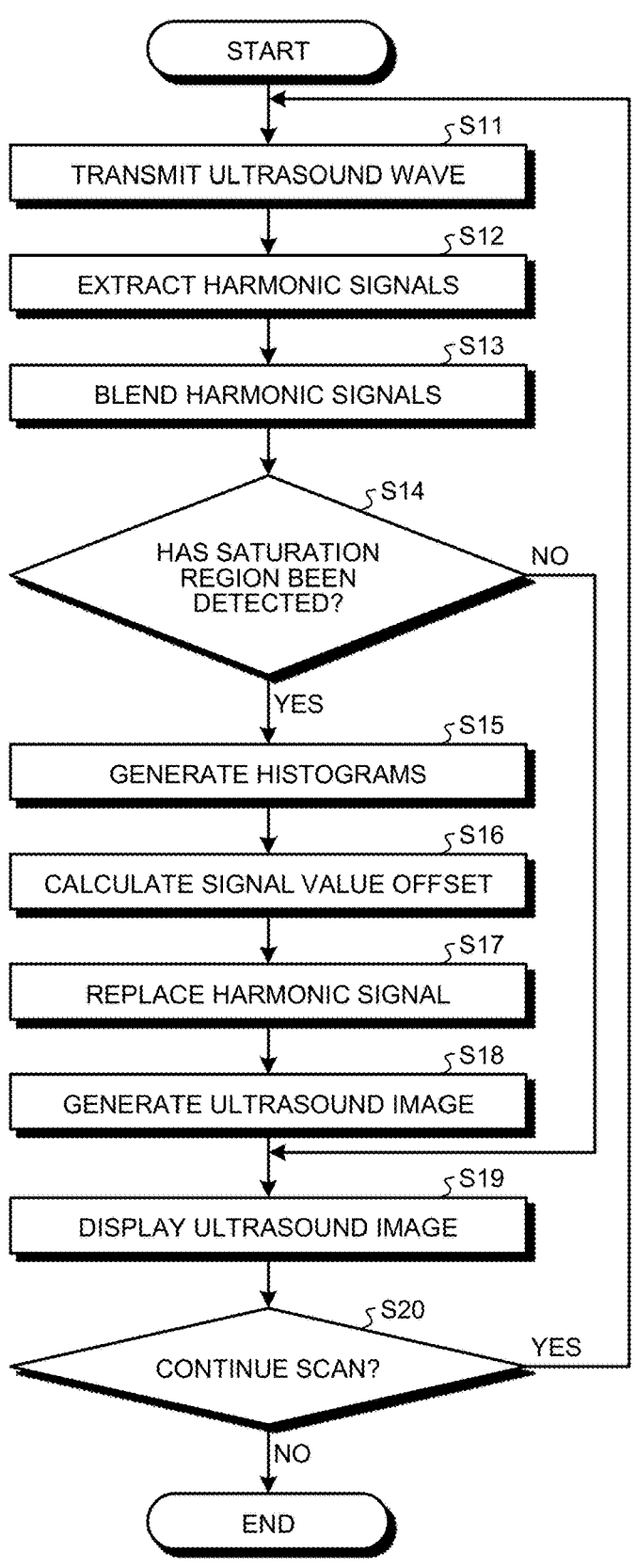
FIG. 14 is a flowchart illustrating an example of processes performed by the ultrasound diagnosis apparatus according to the second embodiment.

Next, processes performed by the ultrasound diagnosis apparatus 1*a* according to the present embodiment will be explained. FIG. 14 is a flowchart illustrating an example of the processes performed by the ultrasound diagnosis apparatus 1*a* according to the present embodiment. Because steps S11 and S12 are the same as those in FIG. 8, explanations thereof will be omitted.

After the second harmonic signal and the third harmonic signal are extracted at step S12, the blending function 118 performs the process of blending the second harmonic signal with the third harmonic signal (step S13). For example, in accordance with the depths, the blending function 118 determines a blending ratio between the second harmonic signal and the third harmonic signal and further generates the blended reflected-wave data by blending together the second harmonic signal and the third harmonic signal extracted at step S12.

Steps S14 through S20 are substantially the same as the processes at steps S3 through S9 in FIG. 8, except that the replacement process is performed on the blended reflected-wave data, and not on the third harmonic component. Thus, explanations thereof will be omitted.

As explained above, the ultrasound diagnosis apparatus 1*a* according to the present embodiment is configured to determine the blending ratio between the second harmonic component and the third harmonic component in accordance with the depths and to generate the blended reflected-wave data by blending the second harmonic component with the third harmonic component. Further, the ultrasound diagnosis apparatus 1*a* according to the present embodiment is configured to perform the same processes as those in the first embodiment on the blended reflected-wave data.

With these arrangements, it is possible to prevent the image quality from being degraded due to the directionality of the second harmonic wave being lower than the directionality of the third harmonic wave when the second harmonic component is used and to also prevent the depth sensitivity from being lowered due to the attenuation of the third harmonic component being larger when the depth is larger. In other words, in addition to advantageous effects similar to those in the first embodiment, the ultrasound diagnosis apparatus 1*a* according to the present embodiment is able to generate an ultrasound image having high image quality while compensating the low depth sensitivity of the third harmonic component.

The embodiments described above may be carried out while being modified as appropriate, by changing a part of the configurations or the functions of the apparatuses. Thus, in the following sections, a number of modification examples related to the above embodiments will be explained as other embodiments. In the following sections, differences from the embodiment described above will primarily be explained. Detailed explanations of some of the features that are the same as those previously explained will be omitted. Further, the modification examples described below may be carried out individually or may be carried out in combination as appropriate.

First Modification Example

In the first and the second embodiments described above, the example was explained in which the process is performed to replace either the signal of the third harmonic component or the signal of the blended reflected-wave data, with the signal based on the second harmonic component, with respect to the saturation region; however, the replacing signal may be an even-numbered order harmonic component other the second harmonic component. For example, the replacing signal may be a fourth harmonic component.

Second Modification Example

In the first and the second embodiments described above, the example was explained in which the process is performed to replace either the signal of the third harmonic component or the signal of the blended reflected-wave data with the signal based on the second harmonic component, with respect to the saturation region; however, the replacing signal may be a signal based on a signal obtained by combining an even-numbered order harmonic component with a harmonic component of order different from that of the even-numbered order harmonic component.

For example, the B-mode processing function 111 (111*a*) may be configured to perform a replacement process by using the third harmonic component as a signal to be replaced and using the blended reflection data as a replacing signal. Furthermore, the B-mode processing function 111 (111*a*) may be configured to perform a replacement process by using the blended reflected-wave data as a signal to be replaced and using blended reflection data blended with a ratio different from that of the replaced signal, as a replacing signal.

According to the present modification example, for example, by using, as the replacing signal, the signal blended by adjusting the ratio between the even-numbered order harmonic component and the odd-numbered order harmonic component, it is possible to more suitably decrease the image degradation caused by the saturation impact component.

The various types of data handled in the present disclosure are, typically, digital data.

According to at least one aspect of the embodiments described above, it is possible to decrease the impacts on the harmonic imaging imposed by the harmonic components occurring from the clamping process.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In relation to the embodiments and the like described above, the following notes are presented as a number of aspects and selected characteristics of the present disclosure.

Note 1

An ultrasound diagnosis apparatus including processing circuitry configured:

to detect a saturation region of a signal based on an ultrasound wave received by an ultrasound probe; and to correct a first signal including an odd-numbered order harmonic component of the saturation region, on the basis of a second signal including an even-numbered order harmonic component of the saturation region.

Note 2

The processing circuitry may be configured to replace the first signal with the second signal.

Note 3

The processing circuitry may be configured to perform a clamping process on an input of the signal based on the ultrasound wave received by the ultrasound probe, so as to suppress a signal level to a prescribed value and may be configured to detect a region of the first signal that became saturated due to the clamping process, as the saturation region.

Note 4

The processing circuitry may be configured to generate odd-numbered order harmonic data and even-numbered order harmonic data on the basis of the ultrasound wave received by the ultrasound probe and may be configured to correct the saturation region included in the odd-numbered order harmonic data, on the basis of the even-numbered order harmonic data of a region corresponding to the saturation region.

Note 5

The first signal may be a signal obtained by combining a first odd-numbered order harmonic component with a harmonic component of order different from that of the first odd-numbered order harmonic component.

Note 6

The second signal may be a signal obtained by combining a first even-numbered order harmonic component with a harmonic component of order different from that of the first even-numbered order harmonic component.

Note 7

The first signal may be a signal obtained by combining a first odd-numbered order harmonic component with a harmonic component of order different from that of the first odd-numbered order harmonic component, whereas the second signal may be a signal obtained by combining a first even-numbered order harmonic component with a harmonic component of order different from that of the first even-numbered order harmonic component.

Note 8

Order of a first odd-numbered order harmonic wave of the first signal and order of a first even-numbered order harmonic wave of the second signal may be consecutive natural numbers.

Note 9

The processing circuitry may be configured to calculate a signal value offset for adjusting the second signal, on the basis of statistical information of the first signal and statistical information of the second signal and may be configured to generate an output signal obtained by replacing the first signal of the saturation region, with a signal obtained by applying the signal value offset to the second signal.

Note 10

The statistical information may be histograms of signal values based on a signal intensity of a reflection signal of the ultrasound wave, and the processing circuitry may be configured to calculate the signal value offset so that an average value of the histogram of the first signal matches an average value of the histogram of the second signal.

Note 11

The statistical information may be histograms of signal values based on a signal intensity of a reflection signal of the ultrasound wave, and the processing circuitry may be configured to calculate the signal value offset on the basis of an average value and a standard deviation of the histogram of the first signal and an average value and a standard deviation of the histogram of the second signal.

Note 12

From an ultrasound image generated on the basis of the first signal, the processing circuitry may be configured to detect, as the saturation region, a region in which a signal value based on a signal intensity of a reflection signal of the ultrasound wave exceeds a threshold value.

Note 13

The processing circuitry may be configured to detect the saturation region, by using a trained model that has learned, through machine learning or deep learning, a relationship between an ultrasound image generated on the basis of the first signal and information indicating the saturation region.

Note 14

An image processing apparatus including processing circuitry configured:

to detect a saturation region of a signal based on an ultrasound wave received by an ultrasound probe; and to correct a first signal including an odd-numbered order harmonic component of the saturation region, on the basis of a second signal including an even-numbered order harmonic component of the saturation region.

Note 15

A computer program product having a computer-readable storage medium including programmed instructions. When executed by a computer, the instructions cause the computer to perform:

detecting a saturation region of a signal based on an ultrasound wave received by an ultrasound probe; and correcting a first signal including an odd-numbered order harmonic component of the saturation region, on the basis of a second signal including an even-numbered order harmonic component of the saturation region.

What is claimed is:

1. An ultrasound diagnosis apparatus, comprising:

an ultrasound probe configured to transmit, to a subject, an ultrasound wave, and receive reflected-wave signals that are based on waves reflected from the subject;

protecting circuitry configured to limit the reflected-wave signals exceeding a predetermined range of amplitudes to within the predetermined range of amplitudes; and processing circuitry configured to:

correct a saturated region represented by a signal limited to within the predetermined range of amplitudes in an odd-numbered order harmonic image obtained from odd-order harmonic components of the reflected wave signal that has passed through the protecting circuitry, by using an even-numbered order harmonic image obtained from even- order harmonic components of the reflected wave signal that has passed through the protecting circuitry, the even-numbered order harmonic image corresponding to the saturated region represented by the odd-numbered order harmonic image, and output the corrected odd-numbered order harmonic image.

2. The ultrasound diagnosis apparatus according to claim 1, wherein the processing circuitry is further configured to generate the odd-numbered order harmonic image based on the odd-numbered order harmonic component of the reflected-wave signals, and the correcting by the processing circuitry includes replacing the saturated region with the corresponding region.

3. The ultrasound diagnosis apparatus according to claim 1, wherein an odd number indicating an order of the odd-numbered order harmonic image and an even number indicating an order of the even-numbered order harmonic image are consecutive natural numbers.

4. The ultrasound diagnosis apparatus according to claim 1, wherein the processing circuitry is further configured to:

generate a first histogram and a second histogram, the first histogram being a histogram of a brightness value of each pixel in the odd-numbered order harmonic image, the second histogram being a histogram of a brightness value of each pixel in the even-numbered order harmonic image, and compare the first histogram to the second histogram to calculate a shift amount for an average of the brightness value of each pixel in the even-numbered order harmonic image that is necessary to match an average of the brightness value of each pixel in the odd-numbered order harmonic image for the first histogram with the average of the brightness value of each pixel on the even-numbered order harmonic image for the second histogram, and set the shift amount to a signal value offset for adjusting the corresponding region, and the correcting by the processing circuitry includes replacing the saturated region included in the odd-numbered order harmonic image with an adjusted region in which the brightness value of each pixel in the corresponding region is offset with the signal value offset.

5. The ultrasound diagnosis apparatus according to claim 4, wherein the processing circuitry is further configured to:

calculate a standard deviation of the brightness value of each pixel in the odd-numbered order harmonic image and a standard deviation of the brightness value of each pixel in the even-numbered order harmonic image, and calculate the average of the brightness value of each pixel in the odd-numbered order harmonic image by taking the standard deviation of the brightness value of each pixel in the odd-numbered order harmonic image into consideration, and calculate the average of the brightness value of each pixel in the even-numbered order harmonic image by taking the standard deviation of the brightness value of each pixel in the even-numbered order harmonic image into consideration.

6. An image processing apparatus, comprising:

processing circuitry configured to:

correct a saturated region represented by a signal limited to within a predetermined range of amplitudes in an odd-numbered order harmonic image obtained from odd-order harmonic components of a reflected wave signal received by an ultrasound probe and has passed through protecting circuitry, by using an even-numbered order harmonic image obtained from even-order harmonic components of the reflected wave signal that has passed through the protecting circuitry, the even-numbered order harmonic image corresponding to the saturated region represented by the odd-numbered order harmonic image; and output the corrected odd-numbered order harmonic image.

7. A computer program product having a non-transitory computer-readable storage medium including programmed instructions, wherein the instructions, when executed by a computer included in an ultrasonic diagnosis apparatus, cause the computer to perform:

correcting a saturated region represented by a signal limited to within a predetermined range of amplitudes in an odd-numbered order harmonic image obtained from odd-order harmonic components of a reflected wave signal that has passed through protecting circuitry, by using an even-numbered order harmonic image obtained from even-order harmonic components of the reflected wave signal that has passed through the protecting circuitry, the even-numbered order harmonic image corresponding to the saturated region represented by the odd-numbered order harmonic image; and outputting the corrected odd-numbered order harmonic image.

8. The ultrasound diagnosis apparatus according to claim 1, wherein the processing circuitry is further configured to generate, based on the reflected-wave signals received by the ultrasound probe, the odd-numbered order harmonic image and the even-numbered order harmonic image that represent a range of the subject to which the ultrasound wave has been transmitted.

9. The ultrasound diagnosis apparatus according to claim 1, wherein the ultrasound probe is configured to transmit, to the subject, the ultrasound wave multiple times corresponding to a plurality of different phases, and receive reflected-wave signals that are based on waves reflected from the subject.

* * * * *